United States Patent [19]

Akasaki et al.

[11] Patent Number: 5,085,960
[45] Date of Patent: Feb. 4, 1992

[54] ELECTROPHOTOGRAPHIC PHOTOSENSITIVE MEMBER AND IMAGE FORMING PROCESS

[75] Inventors: Yutaka Akasaki; Hidekazu Aonuma; Kazuya Hongo; Katsuhiro Sato; Katsumi Nukada; Teruumi Marumo, all of Minami Ashigara, Japan

[73] Assignee: Fuji Xerox Co., Ltd., Tokyo, Japan

[21] Appl. No.: 722,405

[22] Filed: Jun. 20, 1991

Related U.S. Application Data

[63] Continuation of Ser. No. 656,015, Feb. 14, 1991, abandoned, which is a continuation of Ser. No. 416,766, Oct. 4, 1989, abandoned.

[30] Foreign Application Priority Data

May 16, 1988 [JP] Japan .................. 63-116856
Oct. 5, 1988 [JP] Japan .................. 63-249739

[51] Int. Cl.$^5$ ............... G03G 5/047; G03G 5/09
[52] U.S. Cl. .................................. 430/58; 430/59; 430/83; 430/900
[58] Field of Search ............. 430/58, 59, 83, 900

[56] References Cited

U.S. PATENT DOCUMENTS

| 4,184,871 | 1/1980 | Oba et al. ............ 430/83 X |
| 4,818,653 | 4/1999 | Wiedemann et al. ...... 430/900 X |
| 4,835,081 | 5/1989 | Ong et al. ............... 430/59 |

FOREIGN PATENT DOCUMENTS

| 53-20334 | 2/1978 | Japan ................. 430/83 |
| 58-173747 | 10/1983 | Japan ................. 430/58 |
| 59-7956 | 1/1984 | Japan ................. 430/58 |

OTHER PUBLICATIONS

"A New High-Sensitivity Organic Photoconductor for Electrophotography", by R. M. Schaffert, Organic Photoconductor Research and Development, pp. 75-89, Jan. 1971.

Primary Examiner—Roland Martin
Attorney, Agent, or Firm—Finnegan, Henderson, Farabow, Garrett, and Dunner

[57] ABSTRACT

An electrophotographic photosensitive member has a charge-generating layer which includes selected photosensitive pigment particles and a compound which is a tetracyanoanthraquinodimethane compound, an anthraquinone compound, a dicyanovinyl compound, or a special quinone compound. The compound is incorporated in an amount in a range from 0.01 to 2 molar equivalents, preferably 0.1 to 1 molar equivalent, to the pigment, which has a positive hole transporting property. The photosensitive member has a charge-supporting layer and can also have a protective layer. The pigment is a phthalocyanine series pigment, a squearyrium series pigment, or a perylene series pigment. A process of using the photosensitive member includes reversal development and multicolor toner transfer. It is found that the process is adaptable to change in size of the transfer medium.

15 Claims, 1 Drawing Sheet

ELECTROPHOTOGRAPHIC PHOTOSENSITIVE MEMBER AND IMAGE FORMING PROCESS

This application is a continuation of application Ser. No. 07/656,015 filed Feb. 14, 1991, now abandoned, which is a continuation of application Ser. No. 07/416,766, filed Oct. 4, 1989, now abandoned.

CROSS-REFERENCE TO RELATED APPLICATIONS

This application is related to copending, commonly-assigned patent application Ser. No. 07/406,325, filed Sept. 13, 1989 (Yutaka AKASAKI et al.; Attorney Docket No. NGB-847), and to two other concurrently-filed, commonly-assigned patent applications with like titles Ser. No. 07/416,788, now allowed, and Ser. No. 07/416,772.

FIELD OF THE INVENTION

This invention relates to an electrophotographic photosensitive member and an image-forming process using it. More particularly, the invention relates to an electrophotographic photosensitive member having a charge generating layer and a charge transporting layer successively formed on a conductive support.

BACKGROUND OF THE INVENTION

Electrophotographic photosensitive members using an inorganic photoconductive material such as selenium, a selenium alloy, zinc oxide, cadmium sulfide, etc., have been mainly used in the past. However, the electrophotoconductive photosensitive members using inorganic photoconductive materials have problems with respect to producibility, production cost, flexibility, etc.

Recently, for solving such problems, organic photoconductive materials have been vigorously pursued; and electrophotographic photosensitive members using a charge-transfer complex composed of polyvinyl carbazole and 2,4,7-trinitrofluorenone and electrophotographic photosensitive members using an eutectic complex of a pyryrium salt and alkylidenediarylene are known.

Also, most recently, an electrophotographic photosensitive member wherein a function of generating a charge by absorbing light and a function of transporting the charge thus generated are allocated to separate materials is proposed. For example, a double layer or multilayer type electrophotographic photoconductive member separately containing a bisazo pigment and a pyrazoline derivative in these layers is proposed as described in JP-A 58-16247 (the term "JP-A" as used herein means an "unexamined published Japanese patent application").

Furthermore, recently, it is proposed to prevent the increase of a residual potential by incorporating a cyanovinyl compound in a charge transporting layer together with an electron donative charge transfer material as described in JP-A-58-7643.

However, the electrophotographic photosensitive members using these organic photoconductive materials have low photosensitivity and need improvement as photosensitive members. Also, the double layer or multilayer type electrophotographic photosensitive member wherein functions are allocated to a charge generating layer and a charge transporting layer also needs improvement to obtain satisfactory characteristics for practical use.

That is, in the double layer type electrophotographic photosensitive member having a charge generating layer and a charge transporting layer successively formed on a support, the photosensitivity is relatively low; and there are problems that the photosensitivity and the charging potential are undesirably changed by changes in the environmental conditions and also that the potential cycle changes in the light-exposed portions whenever unexposed portions are large.

These problems are also seen in an ordinary process of transferring toner images formed by toner-developing non-exposed portions on a photosensitive member onto a transfer material such as a paper but are particularly remarkable in an image-forming process including the steps of uniformly negatively charging a photosensitive member, forming electrostatic latent images by exposing the member to image-bearing radiation, forming toner images by development, and applying thereto a positive charge during the transfer of the toner images. That is, since the potentials at the exposed portions and the unexposed portions of the aforesaid photosensitive member greatly change during a cycle, the density of the transferred images greatly differs between the initial images and later images obtained after making many copies. Also, after making many copies, when transfer papers are changed for transfer papers having a larger size, the transfer density on the portions of the large transfer paper corresponding to the widened portions becomes higher; or fog is formed on such portions.

SUMMARY OF THE INVENTION

The present invention has been made in consideration of the aforesaid circumstances and the object of this invention is to solve the aforesaid problems in conventional techniques.

That is, the object of this invention is to provide an electrophotographic photosensitive member showing good chargeability and having a high photosensitivity, the photosensitivity and the charged potential thereof being stable during changes of surrounding (environmental) conditions and the potentials at the exposed portions and the unexposed portions being stable during making many copies.

Another object of this invention is to provide an electrophotographic photosensitive member which is suitable for use in an image-forming process including the steps of uniformly charging an electrophotographic photosensitive member; after forming electrostatic latent images, attaching negatively charged toners to the low potential portions of the electrostatic latent images to form toner images; and transferring the toner images by applying a charge of a definite polarity.

Still another object of this invention is to provide an electrophotographic image-forming process capable of providing images having a uniform image density without causing large cycle change of potentials in exposed portions and unexposed portions; in the case of an electrophotographic process including the steps of uniformly negatively charging an electrophotographic photosensitive member, thereafter forming electrostatic latent images; attaching negatively charged toners to low potential portions of the electrostatic latent images to form toner images; and transferring the toner images by applying a charge of a definite polarity.

It has now been discovered that the aforesaid objects of this invention can be attained by using an electrophotographic photosensitive member having a charge generating layer and a charge transporting layer successively formed on a support, wherein the charge generating layer contains a charge generating pigment having a positive hole transporting property and at least one of the compounds represented by formula (Ia) and (Ib) shown below in the binder resin thereof.

In accordance with the present invention, there is provided an electrophotographic photosensitive member having a charge generating layer and a charge transporting layer successively formed on a support, wherein the charge generating layer contains a charge generating pigment having a positive hole transporting property and at least one of a ketone compound represented by formula (Ia) shown below, and a cyanovinyl compound represented by formula (Ib) shown below in the binder resin thereof;

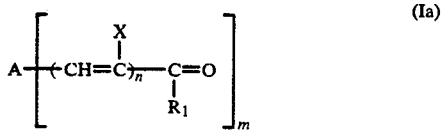

(Ia)

wherein A represents an aromatic group which may be substituted or a heterocyclic group which may be substituted, X represents a hydrogen atom or a halogen atom, $R_1$ represents a hydrogen atom, an alkyl group or a cyano group when n is 0, or a hydrogen atom, an alkyl group, a cyano group or an acryl group when n is 1, n represents 0 or 1, and m represents 1 or 2; and

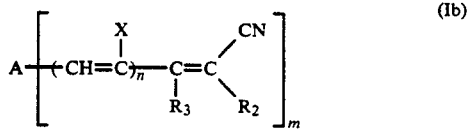

(Ib)

wherein A represents an aromatic group which may be substituted or a heterocyclic group which may be substituted, X represents a hydrogen atom or a halogen atom, $R_2$ represents a cyano group, an aryl group, an alkoxycarbonyl group, an aryloxycarbonyl group, an aminocarbonyl group, an acyl group, a benzoyl group which may be substituted or a phenyl group which may be substituted, $R_3$ represents a hydrogen atom, an alkyl group or a cyano group, n represents 0 or 1, and m represents 1 or 2.

DETAILED DESCRIPTION OF THE INVENTION

The electrophotographic photosensitive member of this invention will now be explained in detail.

FIG. 1 to FIG. 4 each is a schematic sectional view showing the layer structure of the electrophotographic photosensitive member of this invention.

Figure 1:
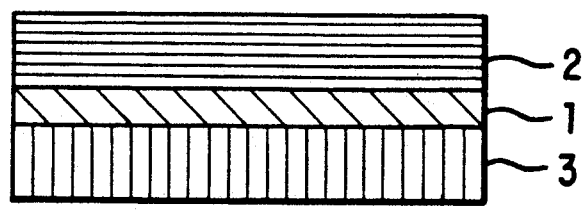
FIG. 1 to FIG. 4 each is a schematic sectional view showing a construction of the electrophotographic photosensitive member of this invention.

In the embodiment of this invention shown in FIG. 1, a charge generating layer 1 and a charge transporting layer 2 are successively formed directly on a conductive support 3.

Figure 2:
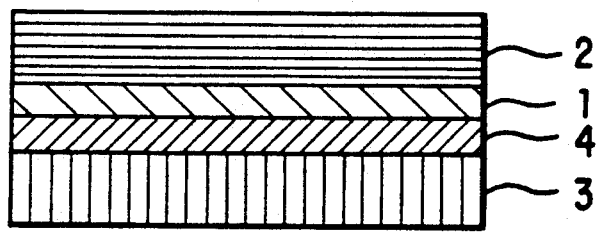

In the embodiment of this invention shown in FIG. 2, an undercoating layer 4 is formed between a conductive support 3 and a charge generating layer 1.

Figure 3:
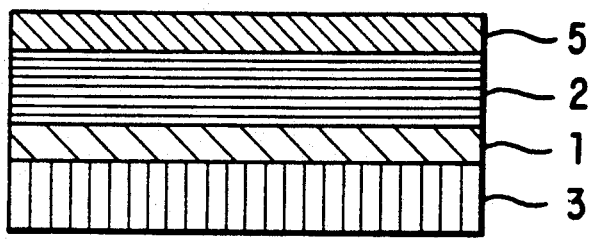

In the embodiment of the invention shown in FIG. 3, a protective layer 5 is formed on the surface of a charge transporting layer 2.

Figure 4:
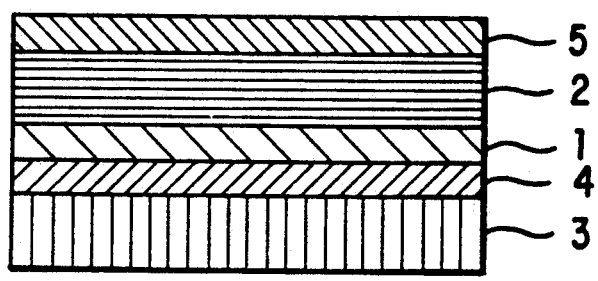

In the embodiment of this invention shown in FIG. 4, an undercoating layer 4 is formed between a conductive support 3 and a charge generating layer 1 and a protective layer 5 is formed on the surface of a charge transporting layer 2.

Now, each layer included in the electrophotographic photosensitive member of this invention will be explained.

As a conductive support 3 for the electrophotographic photosensitive member of this invention, there are a drum of a metal such as aluminum, copper, iron zinc, nickel, etc., and drum-form, sheet-form, or plate-form papers, plastic films or sheets, or glass sheets which are rendered conductive by vapor-depositing thereon a metal film such as any of aluminum, copper, gold, silver, platinum, palladium, titanium, nickel-chromium, stainless steel, copper-indium, etc., or vapor-depositing a conductive metal compound such as a dispersion of any of an indium oxide, tin oxide, etc., or laminating thereon a metal foil, or coating thereon a dispersion of any of carbon black, indium oxide, a tin oxide-antimony oxide powder, a metal powder, etc., in a binder resin.

Furthermore, if necessary, various kinds of treatments can be applied to the surface of a conductive support 3 to overcome adverse bad influences on the image quality. For example, an oxidation treatment, a chemical treatment or a coloring treatment may be applied to the surface of a conductive support or a light absorption layer may be formed on the surface thereof or a light-scattering treatment may be applied onto the surface thereof for preventing the formation of interference fringes and other effect of specular reflection occurring in the case of using coherent light such as laser light, etc., for image-forming exposure. As a method for the light-scattering treatment, a sand blast method, a liquid honing method, a grinding stone polishing method, a buff polishing method, a belt-sander method, a brush polishing method, a steel wool polishing method, an acid etching method, an alkali etching method, an electrochemical etching method, etc. are illustrative.

Also, an undercoating layer 4 may be formed between a conductive support and a charge generating layer 1. The undercoating layer shows actions of inhibiting the injection of charges from the conductive support 3 into the photosensitive layer 1 of the double layer type photosensitive member in charging the photosensitive layer and strongly adhering the photosensitive layer 1 to the conductive support 3 as an adhesive layer or shows an action of preventing the reflection of light on the conductive support.

As the binder resin for the undercoating layer 4, there are polyethylene, polypropylene, an acryl resin, a methacryl resin, a polyamide resin, a vinyl chloride resin, a vinyl acetate resin, a phenol resin, a polycarbonate, polyurethane, a polyimide resin, a vinylidene chloride resin, a polyvinyl acetal resin, a vinyl chloride-vinyl acetate copolymer, polyvinyl alcohol, water-soluble polyester, nitrocellulose, casein, gelatin, etc.

The thickness of the undercoating layer 4 is from 0.01 to 10 μm, and preferably from 0.05 to 3 μm.

As a coating method for forming the undercoating layer, there are a blade coating method, a Meyer bar coating method, a spray coating method, a dip coating method, a bead coating method, an air knife coating method, or a curtain coating method.

The charge generating layer 1 constituting a photosensitive layer on the conductive support 3, or on the undercoating layer 4, in this invention contains a charge generating pigment having a positive hole transporting property, at least one of the ketone compound represented by the above formula (Ia) and the cyanovinyl compound represented by the above formula (Ib) and a binder resin.

According to the present invention, it is required that the charge generating pigment which is used together with at least one of the compounds shown by formulae (Ia) and (Ib) has a positive hole transporting property by itself. Whether or not a charge generating pigment has a positive hole transporting property may be determined by a method comprising: vapor depositing the pigment on a substrate or coating the pigment on a substrate as a dispersion in a resin at a high concentration; charging the layer positively or negatively; and measuring the light decay of the charge. In this invention, the term "charge generating pigment having a positive hole transporting property" means the pigment showing the large light decay for positive charging as compared to the light decay for negative charging in the aforesaid determination method.

As the charge generating pigment having a positive hole transporting property, there are squarylium series pigments, phthalocyanine series pigments, perylene series pigments, etc.

As a first group of specific examples of pigments, from the group of pigments known as the squarylium series pigments, there are those shown by following formula (III)

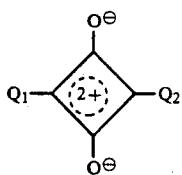

(III)

wherein $Q_1$ and $Q_2$ each represents a substituent selected from those shown by the following formulae:

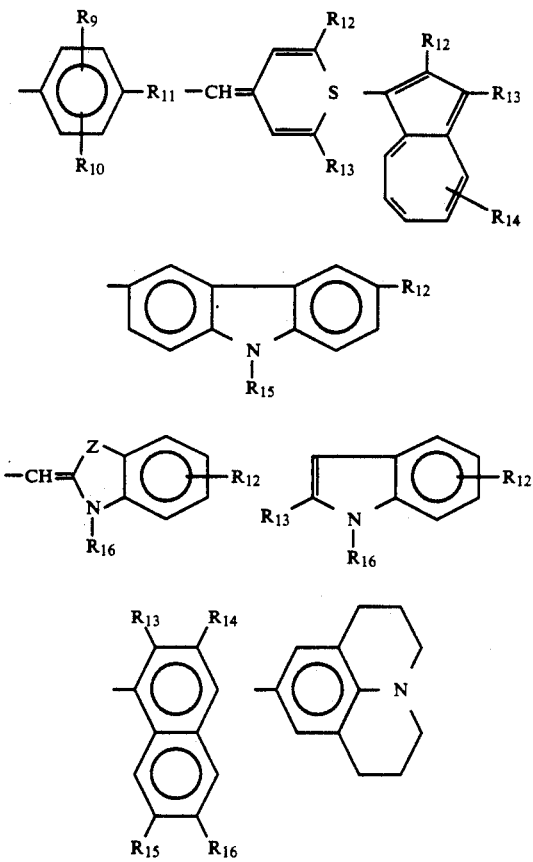

In the above formulae, $R_9$ and $R_{10}$ each represents a hydrogen atom, a hydroxy group, a fluorine atom, an alkyl group, —$NR_{17}R_{18}$ (wherein $R_{17}$ and $R_{18}$ each represents a hydrogen atom, an alkyl group, an aryl group, an aralkyl group, an alkylcarbonyl group, or an arylcarbonyl group), an alkoxy group, or an aryloxy group; $R_{10}$ represents —$NR_{19}R_{20}$ (wherein $R_{19}$ and $R_{20}$ each represents an alkyl group, an aryl group, or an aralkyl group); $R_{12}$ to $R_{15}$ each represents a hydrogen atom, an alkyl group, an aryl group, —$CONHR_{21}$ (wherein $R_{21}$ represents an alkyl group, an aryl group, or an aralkyl group), a halogen atom, an alkoxy group, or an aryloxy group; $R_{16}$ represents an alkyl group, an aryl group, or an aralkyl group; and Z represent >$CR_{22}R_{23}$, —S—, or —$CR_{22}$=$CR_{23}$— (wherein $R_{22}$ and $R_{23}$ each represents a hydrogen atom, an alkyl group, an aryl group, or an aralkyl group).

Specific examples of the squarylium series pigments are illustrated below.

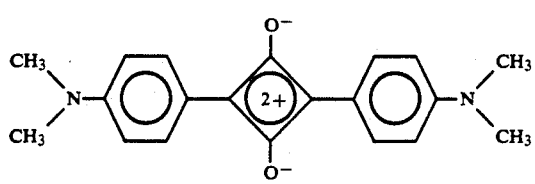

III-1

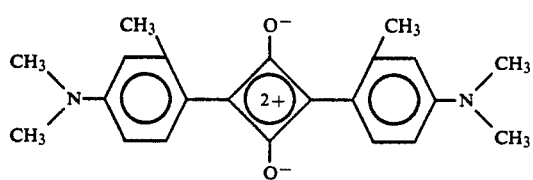
III-2
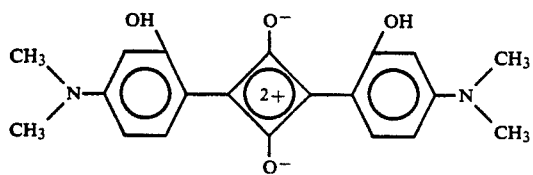
III-3
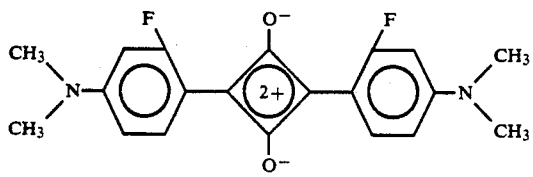
III-4
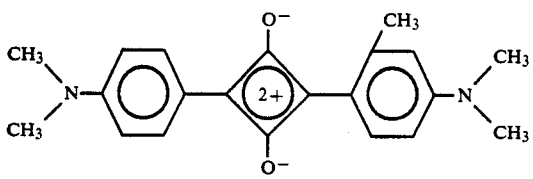
III-5
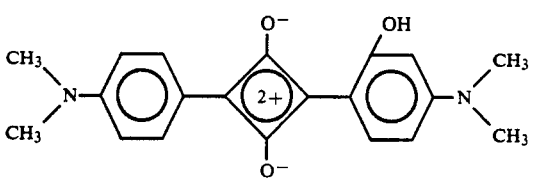
III-6
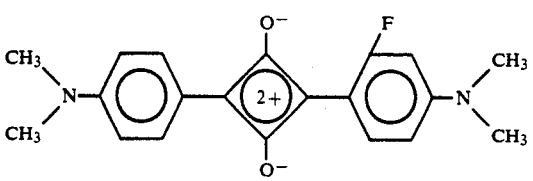
III-7
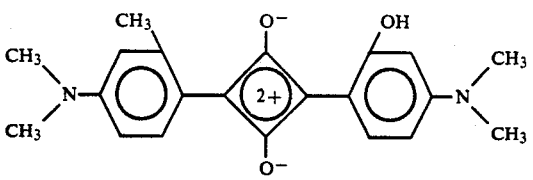
III-8
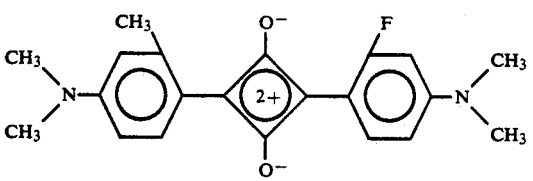
III-9
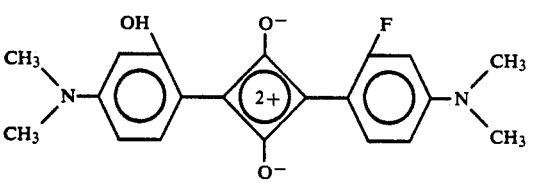
III-10

-continued
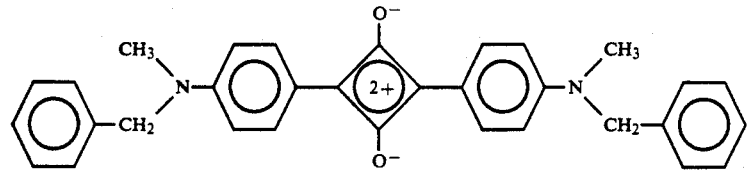
III-11
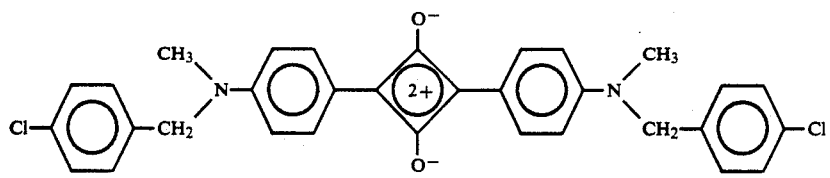
III-12
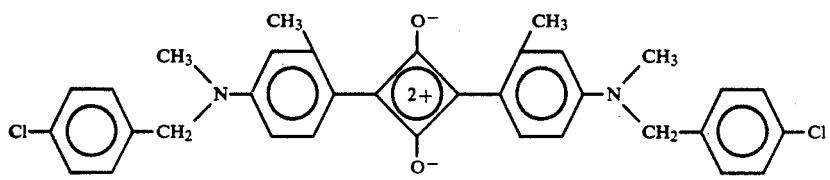
III-13
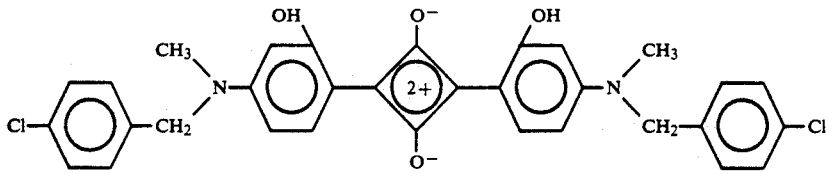
III-14
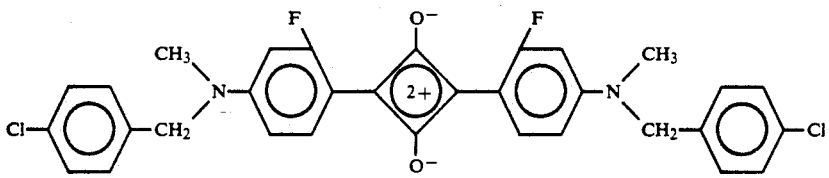
III-15
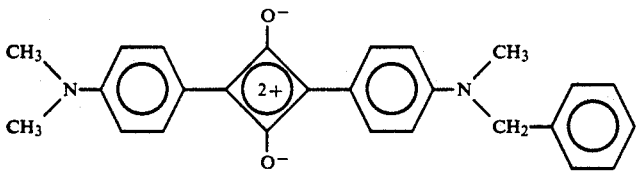
III-16
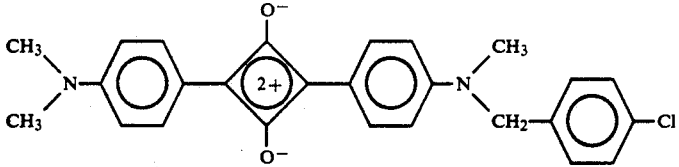
III-17
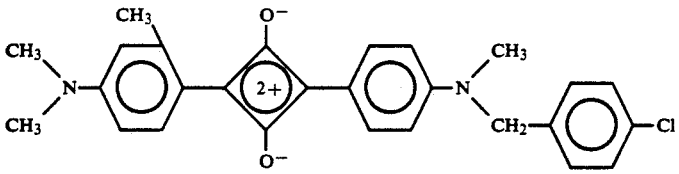
III-18
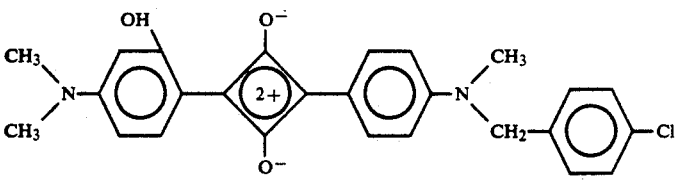
III-19

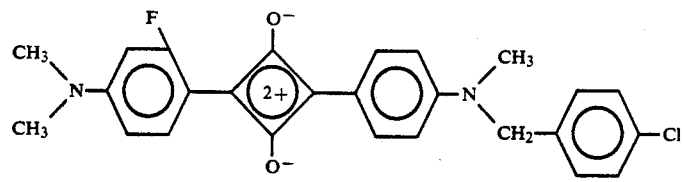
III-20
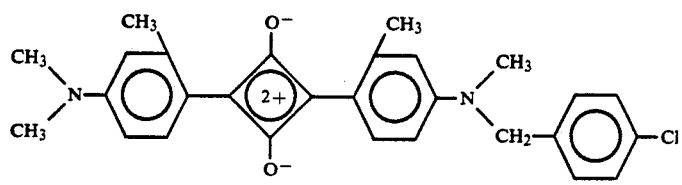
III-21
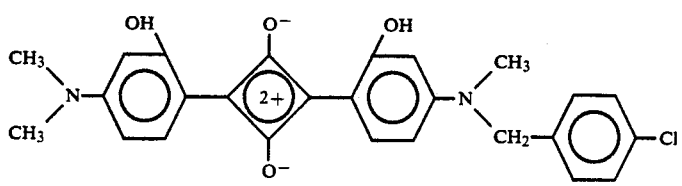
III-22
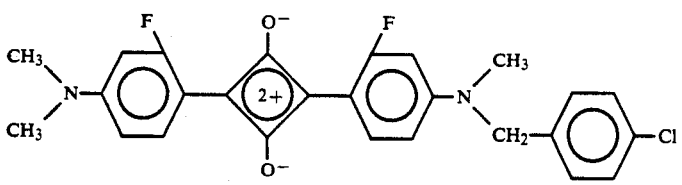
III-23
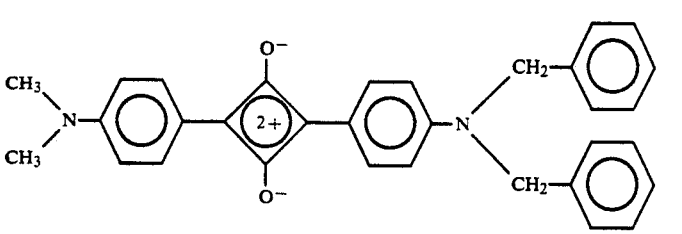
III-24
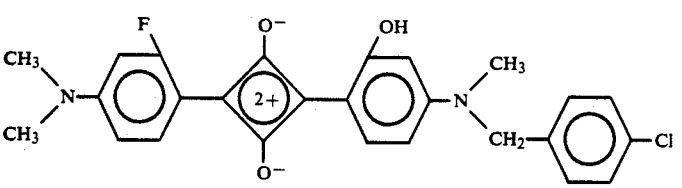
III-25
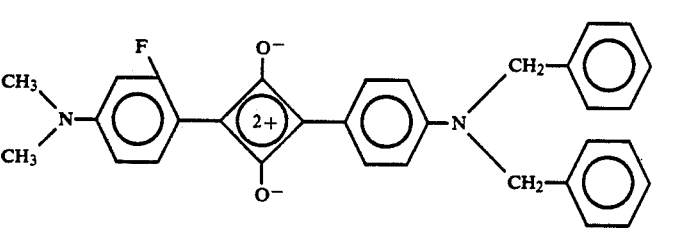
III-26
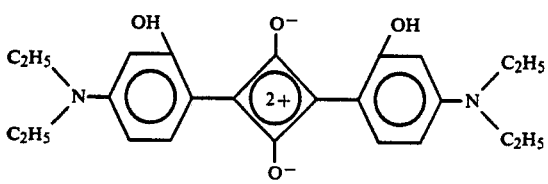
III-27

-continued
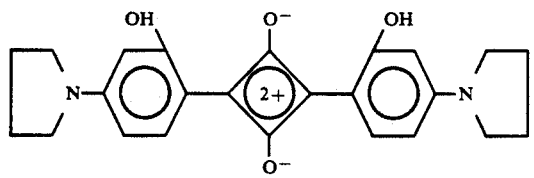
III-28
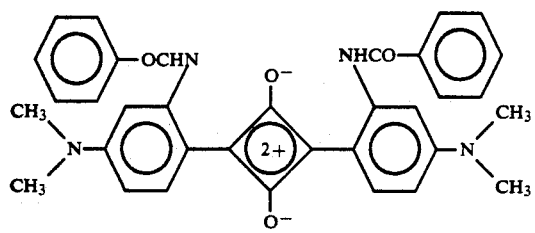
III-29
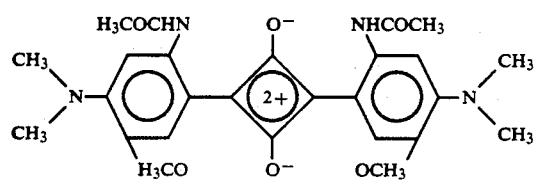
III-30
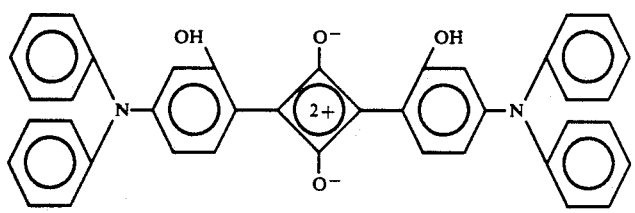
III-31
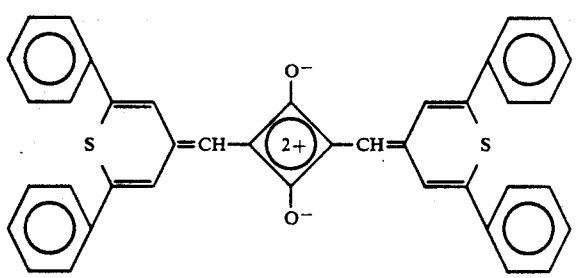
III-32
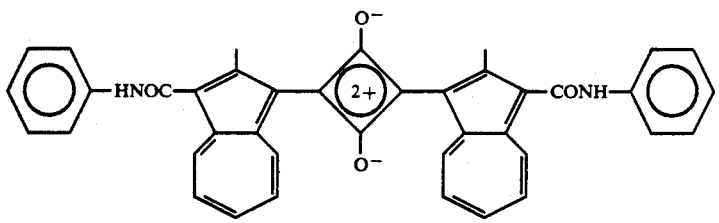
III-33
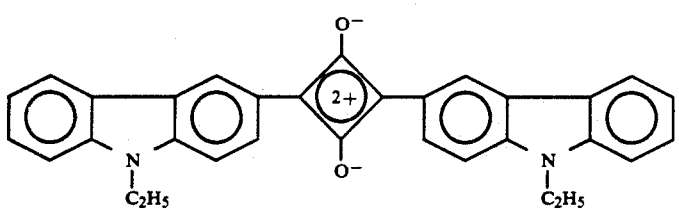
III-34

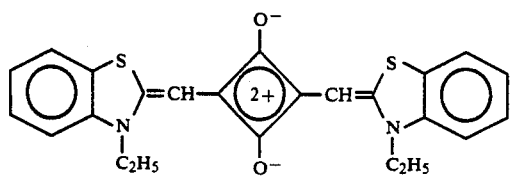
III-35
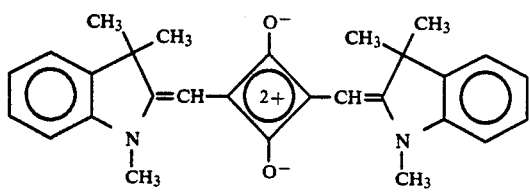
III-36
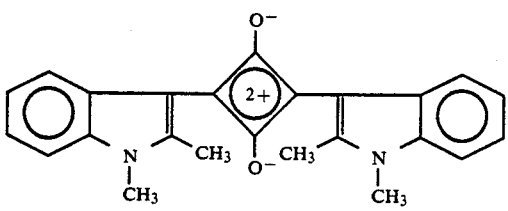
III-37
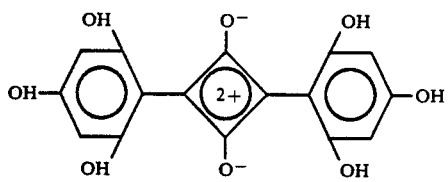
III-38
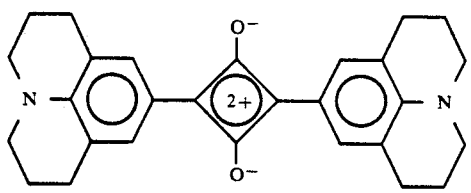
III-39
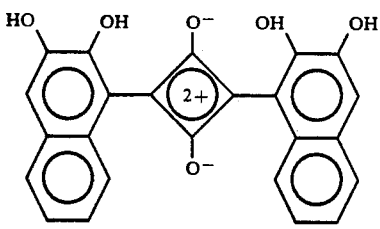
III-40
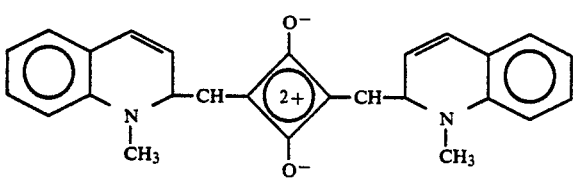
III-41
As a second group of specific examples of pigments, from the group of pigments known as the phthalocyanine series pigments, there are those shown by following formula (IV)

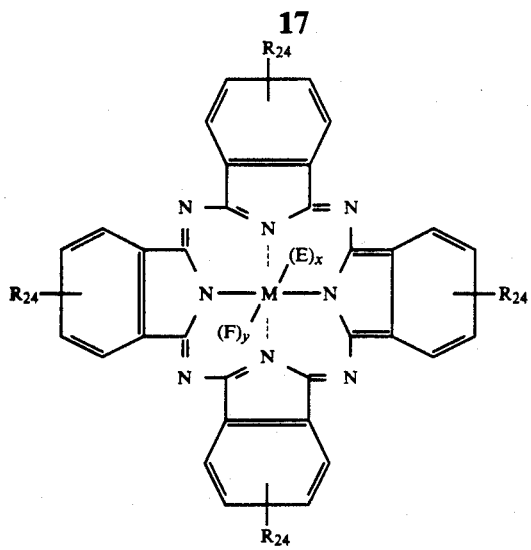

(IV)

wherein $R_{24}$ represents a hydrogen atom, an alkyl group, an aryl group, an aralkyl group, a halogen atom, a cyano group, or a nitro group; M represents two hydrogen atoms or a metal atom selected from Cu, Ni, Co, Fe, Mn, Cr, Ti, Ru, Pd, In, Sn, Sb, Zn, Mg, Ga, Ge, As, Si, Hg, Ti, V, U, and Pd; E and F each represents a halogen atom or an oxygen atom; and x and y each represents 0 or 1; however, when M is a divalent metal atom; x and y each shows 0, when M is a trivalent metal atom; x shows 1 and y shows 0, when M is a tetravelent metal atom; x and y each represents 1, when M is V; E shows an oxygen atom, x shows 1, and y shows 0; and when M is V; E and F each represents an oxygen atom and x and y each represents 1.

Specific examples of the pigment are non-metal phthalocyanine, copper phthalocyanine, vanadyl phthalocyanine, titanyl phthalocyanine, aluminum phthalocyanine, gallium phthalocyanine, indium phthalocyanine, thallium phthalocyanine, silicon phthalocyanine, germanium phthalocyanine, tin phthalocyanine, lead phthalocyanine, and the halides of the aforesaid phthalocyanines.

As a third group of specific examples of pigments, from the group of pigments known as the perylene series pigments, there are those shown by following formula (V)

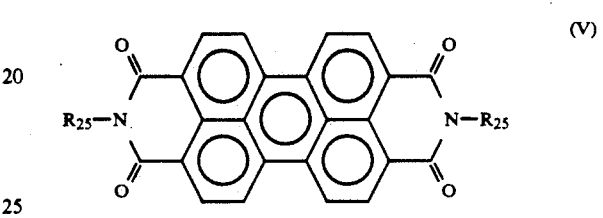

(V)

wherein $R_{25}$ represents an alkyl group, an aryl group, or an aralkyl group, these groups may be substituted.

Specific examples of the perylene pigments are illustrated below.

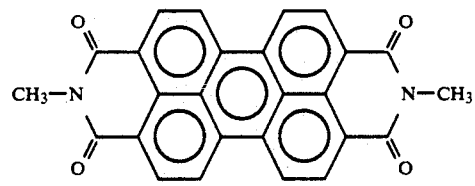

V-1

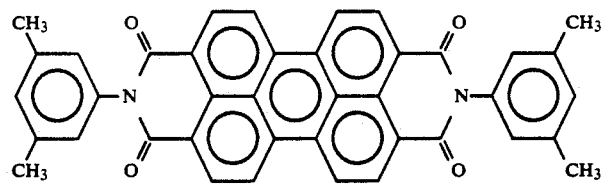

V-2

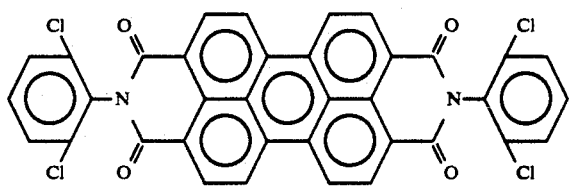

V-3

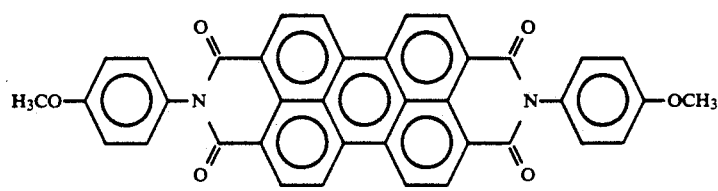

V-4

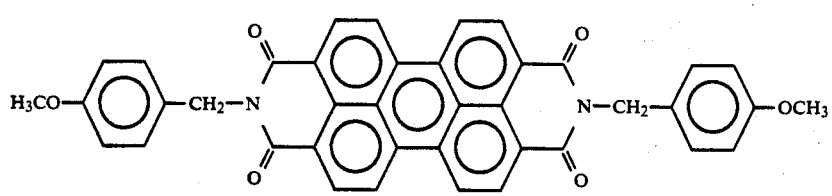
V-5

Of the ketone compounds represented by the formula (Ia) above, compounds which are preferably used in the present invention are those represented by the following formula (IIa):

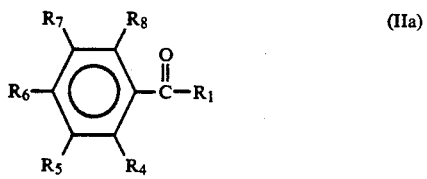
(IIa)

wherein $R_1$ represents a hydrogen atom, an alkyl group or a cyano group, and $R_4$, $R_5$, $R_6$, $R_7$ and $R_8$ each represents a hydrogen atom, an alkyl group, an alkoxy group, an aryloxy group, an aryl group, an alkenyl group, an alkoxycarbonyl group, an aryloxycarbonyl group, an alkylcarbonyl group, an arylcarbonyloxy group, a halogen atom, a cyano group or a nitro group, or two of $R_4$ to $R_8$ which are adjacent to each other form an aromatic ring or a heterocyclic ring.

Specific examples of the ketone compounds, which is deposited with the charge-generating pigment in the charge-generating layer 1, and which is shown by formula (Ia) are illustrated below.

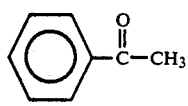
Ia-1

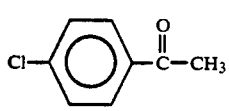
Ia-2

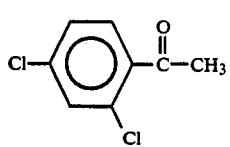
Ia-3

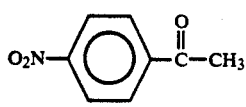
Ia-4

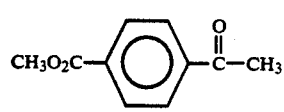
Ia-5

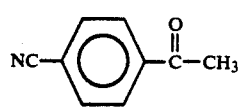
Ia-6

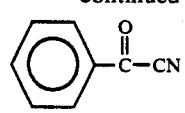
Ia-7

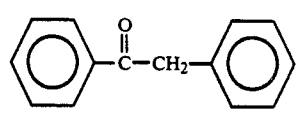
Ia-8

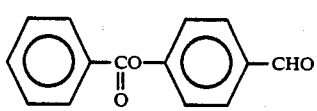
Ia-9

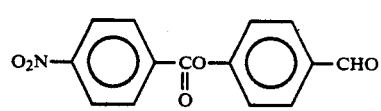
Ia-10

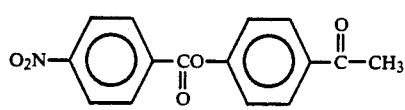
Ia-11

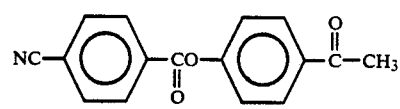
Ia-12

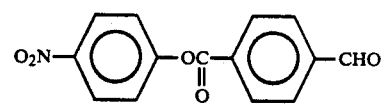
Ia-13

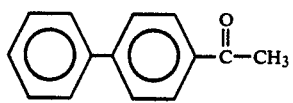
Ia-14

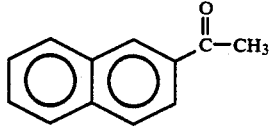
Ia-15

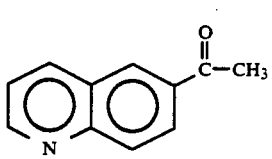
Ia-16

-continued

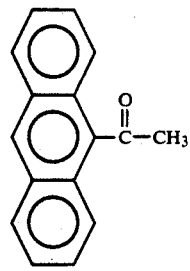 Ia-17

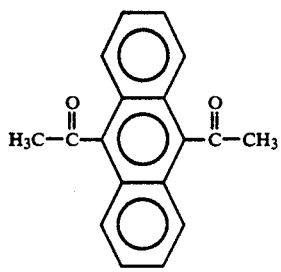 Ia-18

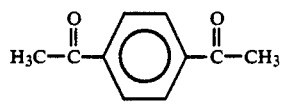 Ia-19

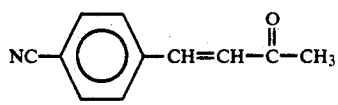 Ia-20

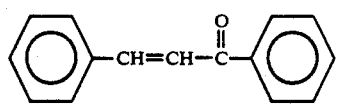 Ia-20

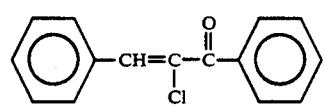 Ia-22

Of the cyanovinyl compounds represented by the formula (Ib) above, compounds which are preferably used in the present invention are those represented by the following formula (IIb)

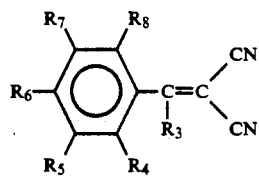 (IIb)

wherein $R_3$ represents a hydrogen atom, an alkyl group or a cyano group, $R_4$, $R_5$, $R_6$, $R_7$ and $R_8$ each represents a hydrogen atom, an alkyl group, an alkoxy group, an aryloxy group, an aryl group, an alkenyl group, an alkoxycarbonyl group, an alkylcarbonyloxy group, an arylcarbonyloxy group, a halogen atom, a cyano group or a nitro group, or an atomic group necessary for forming an aromatic ring or a heterocyclic ring by combining two of $R_4$ to $R_8$ which are adjacent to each other.

Specific examples of the cyanovinyl compound, which is deposited with the charge-generating pigment in charge generating layer 1, and which is shown by formula (Ib) described above, are illustrated below.

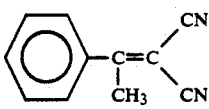 Ib-1

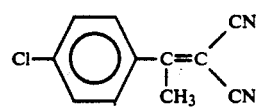 Ib-2

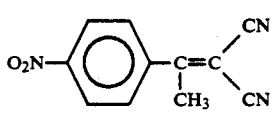 Ib-3

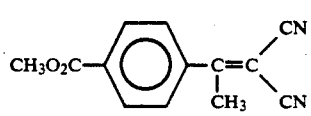 Ib-4

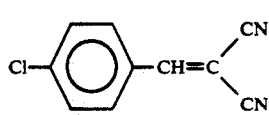 Ib-5

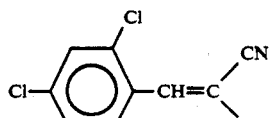 Ib-6

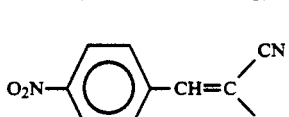 Ib-7

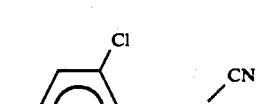 Ib-8

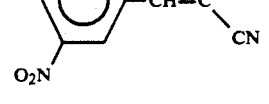 Ib-9

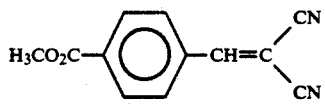 Ib-10

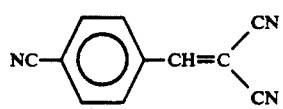 Ib-11

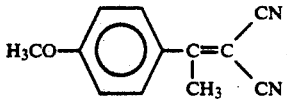 Ib-12

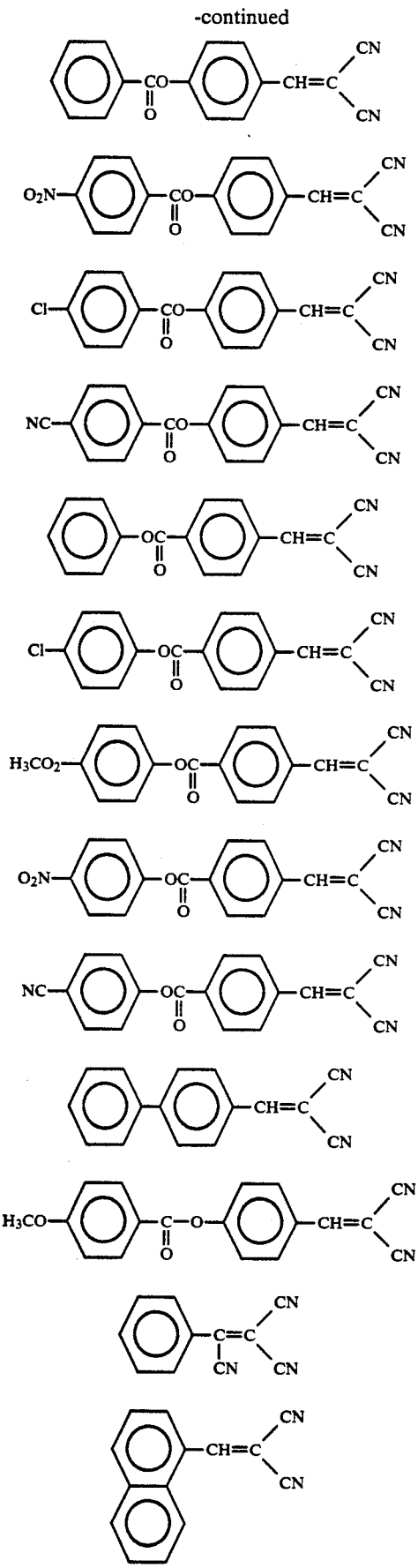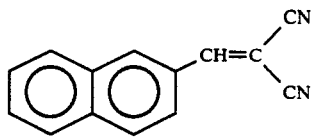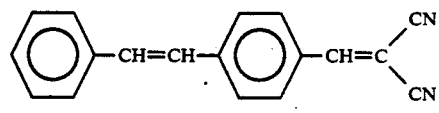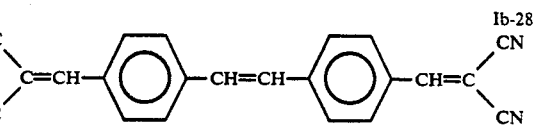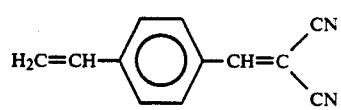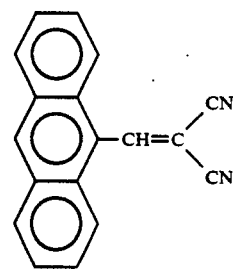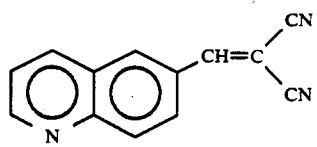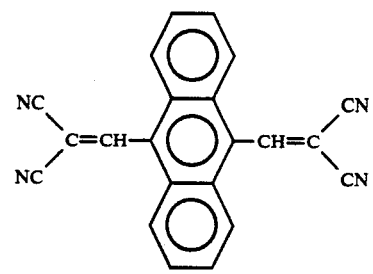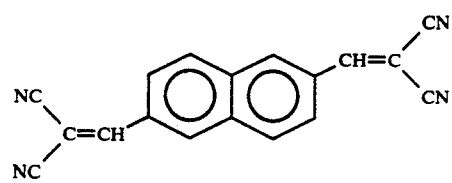

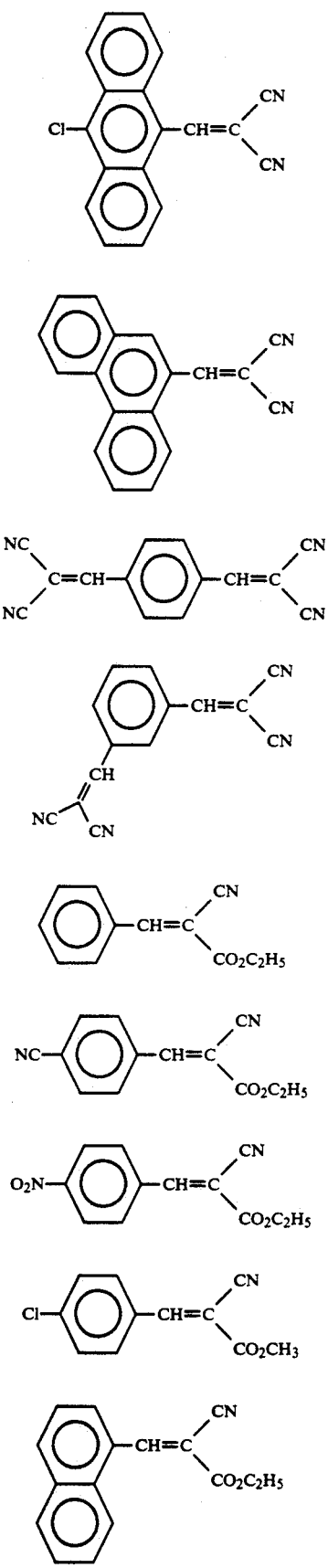

-continued

Ib-54 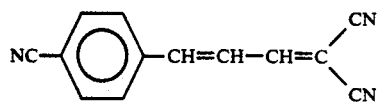

Ib-55 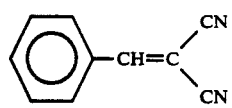

Ib-56 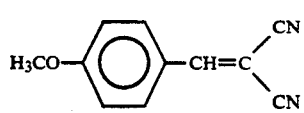

Ib-57 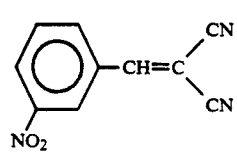

Ib-58 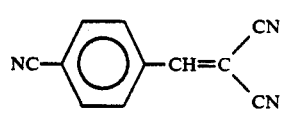

Ib-59 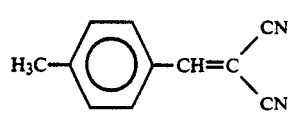

Ib-60 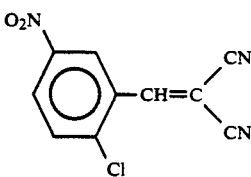

Ib-61 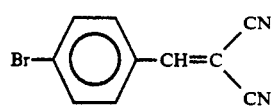

Ib-62 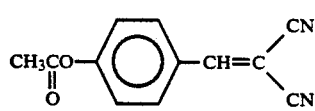

Ib-63 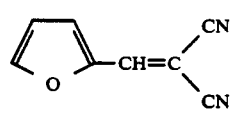

Ib-64 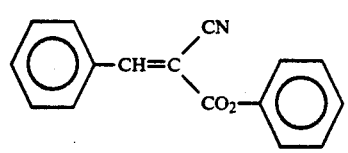

-continued

Ib-65 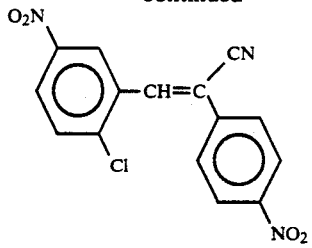

Ib-66 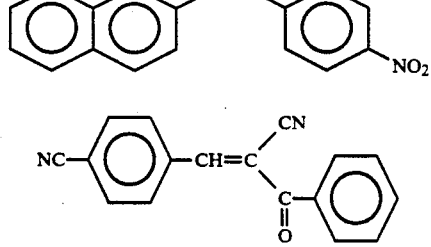

Ib-67 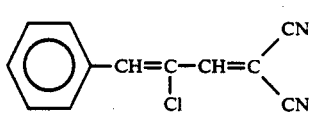

Ib-68 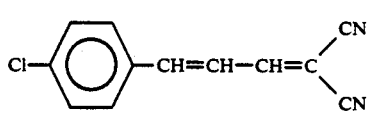

Ib-69 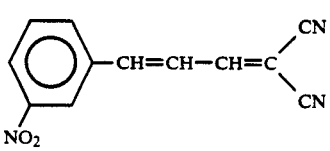

Ib-70 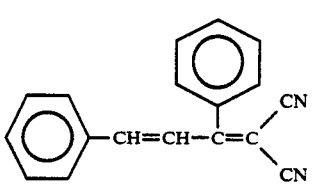

Ib-71 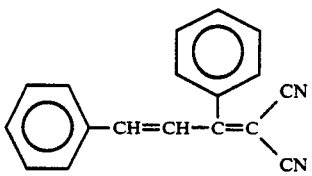

As the binder resin for the aforesaid charge generating pigment having the positive hole transporting property and at least one of the aforesaid compounds shown by formulae (Ia) and (Ib) described above [hereinafter, the compound is referred to as a compound of formula (I)], there are polystyrene, silicone resins, polycarbonate resins, acryl resins, methacryl resins, polyester, vinyl series resins, celluloses, alkyd resins, etc.

In the charge generating layer 1 in this invention, the compound of formula (I) is preferably incorporated therein in the range of from 0.01 to 2 molar equivalents, and preferably from 0.1 to 1 molar equivalent, to the amount of the charge generating pigment having the positive hole transporting property. If the proportion of the compound of formula (I) is less than 0.01 molar equivalent, the aforesaid effects for the increase of photosensitivity and the reduction of the potentials at the exposed portions and unexposed portions by the change of surrounding conditions and by repeated use become less, while if the proportion thereof is over 2 molar equivalents, the dark decay is greatly increased, the charged potential is lowered, and the background portions are liable to be fogged in an electrophotographic process of forming toner images on the unexposed portion. Thus, the aforesaid range is preferred.

Also, it is preferred that the charge generating pigment having a positive hole transporting property is incorporated in the layer in the range of from 0.1 to 10 parts by weight to 1 part by weight of the binder resin.

For incorporating the charge generating pigment having the positive hole transporting property and the compound of formula (I) described above in the charge generating layer 1, various methods can be employed. For example, there are the following methods.

(1) The charge generating pigment having the positive hole transporting property and the compound of formula (I) are dispersed together in a solution of the binder resin in a solvent. As the dispersion method, an ordinary method such as a ball mill dispersion method, an attriter dispersion method, a sand mill dispersion method, a ultrasonic dispersion method, etc., can be used.

(2) The charge generating pigment having the positive hole transporting property is first dispersed in a solution of the binder resin in a solvent and then the compound of formula (I) is added to the dispersion thus formed.

(3) The charge generating pigment having the positive hole transporting property is treated with a solution of the compound of formula (I) to adsorb the compound on the pigment and then the pigment having the compound of formula (I) adsorbed thereon is dispersed in a solution of the binder resin in a solvent.

(4) The charge generating pigment having the positive hole transporting property is dispersed in a solution of the binder resin in a solvent, a film of the dispersion is formed by coating, and then the film is treated with a solution of the compound of formula (I), whereby the film is impregnated with the solution of the compound.

In the case of dispersing the charge generating pigment, it is effective that mean particle size (diameter) of the particles of the charge generating pigment is not larger than 3 µm, and preferably not larger than 0.5 µm.

As the solvent which is used for dispersing the aforesaid component(s), ordinary organic solvents such as methanol, ethanol, n-propanol, n-butanol, benzyl alcohol, methylcellosolve, ethylcellosolve, acetone, methyl ethyl ketone, cyclohexane, methyl acetate, dioxane, tetrahydrofuran, methylene chloride, chloroform, etc., can be used singly or as a mixture thereof.

As a coating method for forming the charge generating layer 1, an ordinary method such as a blade coating method, a Meyer bar coating method, a spray coating method, a dip coating method, a bead coating method, an air knife coating method, a curtain coating method, etc., can be used.

The thickness of the charge generating layer is in the range of generally from 0.05 to 5 µm, and preferably from 0.1 to 2.0 µm.

The charge transporting layer 2 in the electrophotographic photosensitive member of this invention is formed by incorporating a charge transporting material in a proper binder resin.

As the charge transporting material, there are oxadiazole derivatives such as 2,5-bis(p-diethylaminophenyl)-1,3,4-oxadiazole, etc., pyrazoline derivatives such as 1,3,5-triphenylpyrazoline, 1-[pyridyl-(2)]-3-(p-diethylaminostyryl)-5-(p-diethylaminophenyl)pyrazoline, etc., aromatic tertiary amino compounds such as triphenylamine, dibenzylaniline, etc., aromatic tertiary diamino compounds such as N,N'-bis(3-methylphenyl)-[1,1'-bi-phenyl]-4,4'-diamine, etc., 1,2,4-triazine derivatives such as 3-(4'-dimethylaminophenyl)-5,6-di-(4'-methoxy-phenyl)-1,2,4-triaazine, etc., hydrazone derivatives such as 4-diethylaminobenzaldehyde-1,1'-diphenylhydrazone, etc., quinazoline derivatives such as 2-phenyl 4-styryl-quinazoline, etc., benzofuran derivatives such as 6-hydroxy-2,3-di-(p-methoxyphenyl)benzofuran, etc., α-stilbene derivatives such as p-(2,2-diphenylvinyl)-N,N-di-phenylaniline, etc., enamine derivatives described in *Journal of Imaging Science*, Vol. 29, 7–10(1985), carbazole derivatives such as N-ethylcarbazole, etc., poly-N-vinylcarbazole and derivatives thereof, poly-γ-carbazolylethyl glutamate and derivatives thereof and further pyrene, polyvinylpyrene, polyvinylanthracene, polyvinylacrydine, poly-9-biphenylanthracene, a pyreneformaldehyde resin, an ethylcarbazole-formaldehyde resin, etc., although the invention is not limited to them. They can be used singly or as a mixture thereof.

As the binder resin for the charge transporting layer 2, there are polycarbonate resins, polyester resins, polyarylate resins, methacryl resins, acryl resins, vinyl chloride resins, polyvinylacetal resins, a styrene-butadiene copolymer, a vinylidene chloride-acrylonitrile copolymer, a vinyl chloride-vinyl acetate copolymer, a vinyl chloride-vinyl acetate-maleic anhydride terpolymer, silicon resins, silicon-alkyd resins, phenol-formaldehyde resins, styrene-alkyd resins, poly-N-vinylcarbazole, etc., although the invention is not limited to them. These resin binders can be used singly or as a mixture thereof.

The compounding ratio of the charge transporting material to the binder resin is preferably from 10:1 to 1:5 (by weight). The thickness of the charge transporting layer 2 is generally from 5 to 50 µm, and preferably from 10 to 30 µm.

As a coating method for forming the charge transporting layer 2, an ordinary method such as a blade coating method, a Meyer bar coating method, a spray coating method, a dip coating method, a bead coating method, a curtain coating method, etc., can be employed.

Furthermore, as a solvent which is used for forming the charge transporting layer 2, aromatic hydrocarbons such as benzene, toluene, xylene, chlorobenzene, etc., ketones such as acetone, 2-butanone, etc., halogenated hydrocarbons such as methylene chloride, chloroform, ethylene chloride, etc., and cyclic or straight chain ethers such as tetrahydrofuran, ethyl ether, etc., can be used singly or as a mixture thereof.

In the electrophotographic photosensitive member of this invention, if necessary, a protective layer 5 may be formed on the charge transporting layer 2. The protective layer 5 is used for preventing the charge transporting layer 2 from being chemically denatured in charging the photosensitive layer of the multilayer type electrophotographic photosensitive member and for improving the mechanical strength of the photosensitive layer.

The protective layer 5 is formed by incorporating a conductive material in a proper binder resin. As the conductive material, there are metallocene compounds such as N,N'-dimethylferrocene, etc., aromatic amino compounds such as N'N'-diphenyl-N,N'-bis(3-methylphenyl)-(1,1'-phenyl)-4,4'-diamine, etc., and metal oxides such as antimony oxide, tin oxide, titanium oxide, indium oxide, tin oxide-antimony oxide, etc.

Also, as the binder resin for the protective layer 5, there are polyamide resins, polyurethane resins, polyester resins, epoxy resins, polyketone resins, polycarbonate resins, polyvinylketone resins, polystyrene resins, polyacrylamide resins, etc.

The thickness of the protective layer 5 is generally from 0.5 to 20 $\mu$m, and preferably from 1 to 10 $\mu$m.

The electrophotographic photosensitive member of this invention can be used for a known electrophotographic image-forming process. That is, the photosensitive member can be used for an image-forming process including the steps of uniformly charging the surface of a photosensitive member, applying an image exposure thereto to form electrostatic latent images, and developing the latent images by statically charged toner particles, and transferring the developed images to yield copied images having relatively stable image density.

However, the electrophotographic photosensitive member of this invention is particularly suitably used for an image-forming process of forming images by a reversal development process as described below.

That is, the electrophotographic photosensitive member of this invention is particularly suitable for the image-forming process comprising uniformly negatively charging the surface of the electrophotographic photosensitive member, applying thereto an image exposure (electrophotographic exposing radiation) to form electrostatic latent images, attaching negatively charged toners to low-potential portions (exposed portions) of the electrostatic latent images to form toner images, superposing a transfer material on the electrophotographic photosensitive member carrying the toner images thus formed, and applying a positive charge to the photosensitive member from the back surface of the transfer material to transfer the toner images onto the transfer material.

Now, the image-forming process to which the electrophotographic photosensitive member of this invention is applied will be explained.

As a means for uniformly charging the surface of the photosensitive member, a corona discharging device such as corotron, scorotron, di-corotron, pin-corotron, etc., or a charging roller can be used. The initial charging potential is preferably set in the range of from $-700$ volts to $-200$ volts.

As an image exposure means, an illuminating optical system composed of an illumination lamp and an image focusing optical system, a laser exposure optical system composed of a laser light generating source and a laser light deflection device, an LED array, a liquid crystal light bulb, a vacuum fluorescent tube array, an optical fiber array, a light wave guide array, etc., can be desirably used but the use of a light source emitting light having wavelengths in the spectral sensitive region of the photosensitive member is preferred.

The electrostatic latent images formed by the image exposure are developed using a developer to form toner images. As the developer, a two-component developer composed of carrier and toner or a one-component developer composed of toner only can be used. The toner particles may be magnetic toners containing a magnetic powder or may be non-magnetic toners.

In the development, toner particles are allowed to approach the latent images or are brought into a device having a developer carrier containing the developer to attach the toner particles to the electrostatic latent images according to the potential of the latent images.

In this case, according to the charging polarity of the toners, the toners attach to low-potential portions (exposed portions) of the electrostatic latent images on the photosensitive member (negative development) or attach to high-potential portions (unexposed portions) of the electrostatic latent images (positive development). The developing mode can be practiced by selecting the charging polarity of toners being used. Since the electrophotographic photosensitive member of this invention has essentially a negative-charging property, toners of negatively charging property are selected in the case of the negative development and toners of a positive-charging property are selected in the case of the positive development.

During development, a bias voltage can be applied between the support of the electrophotographic photosensitive member and the developer carrier of the developing device. The bias voltage can be a direct current voltage or an alternating current voltage formed by overlapping direct current voltages (a square wave voltage). In particular, in the case of performing the negative development, it is necessary to use a bias voltage the same as or lower in magnitude than the potential at the unexposed portions.

The toner images formed by the development can be transferred onto a transfer material by an optional method. As the transferring means, the aforesaid corona discharging device as well as a transfer roll, a press roll, etc., applied with a transfer voltage can be used but an electric field transfer performing the transfer by applying a charge to the photosensitive member from the back surface of the transfer material is effective. For example, in the case of negatively charged toner particles of the toner images formed by the negative development, the toner images are suitably transferred onto the transfer material by applying a positive corona discharge from the back surface of the transfer material.

After the transfer of the toner images is finished, the photosensitive member is, if necessary, cleaned to remove remaining toner images (untransferred toner images) and then the charges on the photosensitive member are discharged by means of an erase lamp or a corotron for a subsequent image-forming step.

The electrophotographic photosensitive member of this invention can be suitably used in a so-called one pass multicolor image forming process.

For example, the electrophotographic photosensitive member can be suitably used for an image forming process by applying a first image exposure to form first electrostatic latent images; attaching negatively charged toners to low potential portions of the first electrostatic latent images to form first toner images; then, applying a second image exposure to form second electrostatic latent images; attaching positively charged second toners to high-potential portions of the second electrostatic latent images to form second toner images; after unifying the polarities of the first toner images and the second toner images to the polarity of one of both the toner images, superposing a transfer material on the electrophotographic photosensitive member carrying the first and second toner images; and applying a charge of an opposite polarity to the polarity of the first and second toner images from the back surface of the transfer material to transfer the first and second toner images onto the transfer material.

In the aforesaid one-pass multicolor image forming process, as a means for uniformly charging the photosensitive member, an image exposure means, a developing means, and a transferring means, the aforesaid means can be similarly used, as follows.

First, the surface of the photosensitive member is uniformly charged and then a first image exposure is applied. For the first image exposure, an image portion exposure for exposing appropriate portions of the photosensitive member corresponding to selected image portions is employed. The first electrostatic latent images formed are developed using a first developer to form first toner images. In this case, negatively charged first toners are attached to low-potential portions (exposed portions) of the first electrostatic latent images using a developer carrier of a developing device applied with a bias voltage of a lower potential than the initially charged potential to form first toner images.

Then, a second image exposure is performed and, for the second image exposure, a background portion exposure for exposing the portions of the photosensitive member corresponding to non-image portions is employed. In the second image exposure, it is preferred to use a light source having an intensity weaker than that of the light source used for the first image exposure and to expose in such a manner that the potential of the portions of the photosensitive member corresponding to the background portions reduces to almost a half of the initial charging potential.

Then, positively charged second toners are attached to the portions not exposed in the second image exposure (the selected image portion for the second image exposure). In this case, it is preferred to perform the development by second toners carried on a developer carrier applied with a bias voltage of a higher potential than the potential of the portions of the photosensitive member corresponding to the background portions. Also, since the second development is a so-called overlapping development of applying the development onto the photosensitive member already having thereon the first toner images, it is preferred to use a two-component developer composed of a toner and a negatively charged low-density carrier during the second development for preventing the occurrence of the disturbance of the first toner images and the entrance of the first toners in the developed second toner. Also, a carrier having a density of less than 4.0 g/cm$^2$ is preferred.

After forming the first toner images and the second toner images on the photosensitive member, these toner images are transferred onto a transfer material. In this case, since these toners are charged in opposite polarities to each other, it is necessary unify these polarities to one of the polarities. For unifying the polarities, corona discharging by a charging device is applied before the transfer. In this case, since the electrophotographic photosensitive member of this invention has a negative-charging property, it is preferred to unify the polarities to a positive polarity. For charging before the transfer, it is preferred to use an alternating current voltage formed by overlapping positive direct current voltages (square wave voltages).

Then, a transfer material is superposed on the toner images on the photosensitive member and a charging potential having a polarity opposite to the polarity of the toner images, e.g., of a negative polarity in the case of toner images unified to a positive polarity is applied to the photosensitive member from the back surface of the transfer material to transfer the toner images onto the transfer material. In this case, it is preferred to use a negative direct current voltage as the transfer potential.

The image-forming is performed as described above in this invention and, in this case, toners each having a different proper color can be used for the first and the second toners. For example, when the electrophotographic photosensitive member is a drum form, two-color images can be obtained during one rotation of the drum.

Then, the electrophotographic photosensitive member of this invention and the image-forming process using it are described practically by the following examples.

EXAMPLE 1

The surface of an aluminum pipe of 40 mm in outer diameter and 319 mm in length subjected to mirror plane cutting was treated by buff polishing such that the surface roughness Ra became 0.17 $\mu$m. Then, a mixture having the following composition was prepared for forming an undercoating layer 4.

| | |
|---|---|
| Polyamide Resin (Luckermide 5003, trade name, made by Dainippon Ink and Chemicals, Inc.) | 1 part by weight |
| Methanol | 5 part by weight |
| n-Butanol | 3 part by weight |
| Water | 1 part by weight |

The aforesaid mixture was coated on the aluminum pipe by dip coating and dried for 10 minutes at 110° C. to form an undercoating layer 4 of 1 $\mu$m in thickness.

Then, a mixture of the following composition was prepared.

| | |
|---|---|
| X-Type Non-Metal Phthalocyanine (charge generating pigment) | 1 part by weight |
| Ketone Compound (Compound Ia-10) | 0.3 molar equivalent to the pigment |
| Polyvinyl Butyral Resin (BM1, trade name, made by Sekisui Chemical Co., Ltd.) | 1 part by weight |
| Cyclohexane | 60 part by weight |

The aforesaid mixture was dispersed for 10 minutes by a sand mill using glass beads of 1 mm in diameter to provide a dispersion of the pigment having a mean particle size of about 0.05 $\mu$m. The dispersion obtained was coated on the aforesaid undercoating layer by dip coating and dried by heating to 120° C. for 10 minutes to form a charge generating layer 1 of 0.25 $\mu$m in thickness.

Furthermore, a mixture of the following composition was prepared.

| | |
|---|---|
| N,N'-Diphenyl-N,N'-bis(3-methylphenyl)-[1,1'-biphenyl]-4,4'-diamine | 2 parts by weight |
| Polycarbonate Resin (bisphenol Z type) | 3 parts by weight |
| Monochlorobenzene | 20 parts by weight |

The aforesaid mixture was coated on the charge generating layer 1 by dip coating and dried for 60 minutes at 110° C. to form a charge transporting layer 2 of 20 $\mu$m in thickness.

The electrophotographic photosensitive member thus prepared was negatively charged using Scorotron (grid voltage: −300 volts), exposed to semiconductor laser (780 n.m. oscillation) to cause light decay; after exposure, a probe of a surface potentiometer was placed on a position after 0.3 second (corresponding to the position after 0.6 second since charging), and the potential (VH) for non-exposure and the potential (VL: 30 erg/cm$^2$ exposure) for exposure were measured. Furthermore, Corotron (wire voltage: +5.0 KV) was disposed at the rear of the probe and the photosensitive member was positively charged. Thereafter, the charges were removed by a tungsten lamp.

In the system, the step of negative-charging exposure, positive-charging exposure for charge removal was defined as one cycle and the changes of VH and VL up to 200 cycles were measured. The measurement was carried out under the surrounding conditions of 32° C., 85% RH; 20° C., 55% RH; and 10° C., 15% RH. The results obtained are shown in Table 1.

Also, the electrophotographic photosensitive member described above was mounted on a laser printer (XP-11, trade name, made by Fuji Xerox Co., Ltd.). After continuously making 500 prints using A4 size (210 mm × 297 mm) papers, printing was carried out using B4 size (257 mm × 364 mm) papers only; and the density difference of printout between the A4 size paper portion and the widened portion by B4 size paper and the fog at the background portions in each portion were evaluated under the condition of 32° C., 85% RH. The results obtained are shown in Table 2.

In addition, in the laser printer, magnetic one-component toners of a negative polarity were used as the developer and also the toner images attached to the exposed portions of the photosensitive member were trasnferred by transfer Corotron of a DC voltage of +4.8 KV.

EXAMPLES 2 to 7

By following the same procedure as Example 1 except that the amount of the ketone compound (Compound Ia-10) was changed to 0.005 molar equivalent (Example 2), 0.01 molar equivalent (Example 3), 0.1 molar equivalent (Example 4), 1.0 molar equivalent (Example 5), 2.0 molar equivalents (Example 6), or 4.0 molar equivalents (Example 7) to the pigment, electrophotographic photosensitive members were prepared and the same evaluations as above were made on each sample. The results obtained are shown in Table 1 and Table 2 below.

EXAMPLES 8 to 25

By following the same procedure as Example 1 except that other compounds of formula (I) (i.e., the compounds of (Ia) or (Ib)) shown in Tables 1 and 2 were used in place of the ketone compound (Ia-10) in the amounts shown in the tables, electrophotographic photosensitive materials were prepared and the same evaluations as above were made on each sample. The results obtained are shown in Table 1 and Table 2.

COMPARISON EXAMPLE 1

By following the same procedure as Example 1 except that the ketone compound was not added and the same evaluation was made. The results are shown in Table 1 and Table 2 below.

TABLE 1

(Unit: volt)

| | No. | Amount (equivalent) | | 32° C., 85% RH at one cycle | 32° C., 85% RH at 200 cycles | 20° C., 55% RH at one cycle | 20° C., 55% RH at 200 cycles | 10° C., 15% RH at one cycle | 10° C., 15% RH at 200 cycles |
|---|---|---|---|---|---|---|---|---|---|
| | Ketone compound (Ia) | | | | | | | | |
| Example 1 | Ia-10 | 0.3 | VH | −251 | −249 | −258 | −256 | −262 | −260 |
| | | | VL | −54 | −54 | −56 | −55 | −59 | −60 |
| Example 2 | Ia-10 | 0.005 | VH | −231 | −214 | −253 | −244 | −281 | −284 |
| | | | VL | −61 | −39 | −75 | −69 | −101 | −102 |
| Example 3 | Ia-10 | 0.01 | VH | −248 | −245 | −255 | −249 | −261 | −260 |
| | | | VL | −58 | −52 | −60 | −57 | −67 | −67 |
| Example 4 | Ia-10 | 0.1 | VH | −251 | −249 | −256 | −252 | −259 | −260 |
| | | | VL | −56 | −55 | −59 | −57 | −62 | −61 |
| Example 5 | Ia-10 | 1.0 | VH | −247 | −246 | −249 | −247 | −251 | −252 |
| | | | VL | −50 | −49 | −53 | −52 | −55 | −55 |
| Example 6 | Ia-10 | 2.0 | VH | −209 | −208 | −213 | −209 | −217 | −215 |
| | | | VL | −42 | −41 | −45 | −44 | −46 | −47 |
| Example 7 | Ia-10 | 4.0 | VH | −140 | −140 | −157 | −152 | −163 | −165 |
| | | | VL | −37 | −37 | −39 | −38 | −41 | −42 |
| Example 8 | Ia-6 | 0.3 | VH | −253 | −252 | −256 | −255 | −259 | −260 |
| | | | VL | −50 | −49 | −53 | −52 | −58 | −59 |
| Example 9 | Ia-16 | 0.3 | VH | −249 | −249 | −251 | −250 | −253 | −254 |
| | | | VL | −50 | −49 | −51 | −51 | −54 | −53 |
| Example 10 | Ia-18 | 0.3 | VH | −251 | −250 | −260 | −259 | −265 | −265 |
| | | | VL | −49 | −48 | −55 | −53 | −59 | −58 |
| Example 11 | Ia-20 | 0.3 | VH | −249 | −250 | −254 | −254 | −259 | −260 |
| | | | VL | −50 | −49 | −54 | −52 | −58 | −60 |
| | Cyanovinyl Compound (Ib) | | | | | | | | |
| Example 12 | Ib-14 | 0.3 | VH | −250 | −248 | −255 | −254 | −262 | −260 |
| | | | VL | −53 | −50 | −53 | −53 | −52 | −52 |
| Example 13 | Ib-14 | 0.005 | VH | −230 | −205 | −256 | −225 | −282 | −290 |
| | | | VL | −65 | −35 | −89 | −75 | −100 | −105 |
| Example 14 | Ib-14 | 0.01 | VH | −233 | −221 | −255 | −231 | −280 | −282 |
| | | | VL | −59 | −42 | −70 | −61 | −90 | −95 |
| Example 15 | Ib-14 | 0.1 | VH | −242 | −235 | −253 | −248 | −270 | −272 |
| | | | VL | −55 | −48 | −60 | −55 | −60 | −62 |
| Example 16 | Ib-14 | 1.0 | VH | −245 | −243 | −248 | −245 | −250 | −252 |
| | | | VL | −48 | −45 | −50 | −48 | −52 | −53 |
| Example 17 | Ib-14 | 2.0 | VH | −175 | −170 | −202 | −200 | −210 | −201 |

TABLE 1-continued

|  | No. | Amount (equivalent) |  | 32° C., 85% RH | | 20° C., 55% RH | | 10° C., 15% RH (Unit: volt) | |
|---|---|---|---|---|---|---|---|---|---|
|  |  |  |  | at one cycle | at 200 cycles | at one cycle | at 200 cycles | at one cycle | at 200 cycles |
|  |  |  | VL | −35 | −35 | −40 | −41 | −48 | −46 |
| Example 18 | Ib-14 | 4.0 | VH | −100 | −91 | −150 | −142 | −169 | −159 |
|  |  |  | VL | −30 | −31 | −32 | −33 | −37 | −31 |
| Example 19 | Ib-6 | 0.3 | VH | −248 | −245 | −250 | −253 | −257 | −263 |
|  |  |  | VL | −44 | −48 | −53 | −52 | −56 | −58 |
| Example 20 | Ib-8 | 0.3 | VH | −243 | −241 | −249 | −250 | −258 | −258 |
|  |  |  | VL | −41 | −40 | −47 | −46 | −49 | −52 |
| Example 21 | Ib-10 | 0.3 | VH | −257 | −255 | −261 | −259 | −263 | −264 |
|  |  |  | VL | −59 | −58 | −61 | −60 | −63 | −65 |
| Example 22 | Ib-13 | 0.3 | VH | −241 | −241 | −248 | −247 | −253 | −257 |
|  |  |  | VL | −43 | −41 | −48 | −47 | −55 | −57 |
| Example 23 | Ib-24 | 0.3 | VH | −249 | −245 | −251 | −253 | −257 | −261 |
|  |  |  | VL | −52 | −50 | −57 | −60 | −53 | −67 |
| Example 24 | Ib-30 | 0.3 | VH | −239 | −237 | −245 | −244 | −248 | −253 |
|  |  |  | VL | −43 | −43 | −45 | −44 | −47 | −51 |
| Example 25 | Ib-39 | 0.3 | VH | −249 | −247 | −250 | −252 | −259 | −263 |
|  |  |  | VL | −54 | −53 | −55 | −53 | −59 | −61 |
| Comparison Example 1 | — | — | VH | −220 | −200 | −254 | −245 | −290 | −300 |
|  |  |  | VL | −65 | −30 | −82 | −75 | −110 | −114 |

TABLE 2

|  | No. | Amount (equivalent) | Printout Density Difference Between the Portion Used for A-4 Size Paper and the Widened Portion | Fog at Background Position | |
|---|---|---|---|---|---|
|  |  |  |  | Portion Used for A-4 Size Paper | Widened Portion by B-4 Size Paper |
|  | Ketone compound (Ia) | | | | |
| Example 1 | Ia-10 | 0.3 | Uniform (no difference) | no fog | no fog |
| Example 2 | Ia-10 | 0.005 | * | no fog | fogged |
| Example 3 | Ia-10 | 0.01 | Uniform (no difference) | no fog | no fog |
| Example 4 | Ia-10 | 0.1 | " | no fog | no fog |
| Example 5 | Ia-10 | 1.0 | " | no fog | no fog |
| Example 6 | Ia-10 | 2.0 | " | slightly fogged | slightly fogged |
| Example 7 | Ia-10 | 4.0 | " | fogged | fogged |
| Example 8 | Ia-6 | 0.3 | " | no fog | no fog |
| Example 9 | Ia-16 | 0.3 | " | no fog | no fog |
| Example 10 | Ia-18 | 0.3 | " | no fog | no fog |
| Example 11 | Ia-20 | 0.3 | " | no fog | no fog |
|  | Cyanovinyl compound (Ib) | | | | |
| Example 12 | Ib-14 | 0.3 | Uniform (no difference) | no fog | no fog |
| Example 13 | Ib-14 | 0.005 | * | no fog | fogged |
| Example 14 | Ib-14 | 0.01 | Uniform (no difference) | no fog | no fog |
| Example 15 | Ib-14 | 0.1 | " | no fog | no fog |
| Example 16 | Ib-14 | 2.0 | " | no fog | no fog |
| Example 17 | Ib-14 | 2.0 | " | no fog | no fog |
| Example 18 | Ib-14 | 4.0 | " | slightly fogged | slightly fogged |
| Example 19 | Ib-6 | 0.3 | " | no fog | no fog |
| Example 20 | Ib-8 | 0.3 | " | no fog | no fog |
| Example 21 | Ib-10 | 0.3 | " | no fog | no fog |
| Example 22 | Ib-13 | 0.3 | " | no fog | no fog |
| Example 23 | Ib-24 | 0.3 | " | no fog | no fog |
| Example 24 | Ib-30 | 0.3 | " | no fog | no fog |
| Example 25 | Ib-39 | 0.3 | " | no fog | no fog |
| Comparison Example 1 | — | — | " | no fog | fogged |

*The pintout density in the widened portion was higher than that in the portion used for A-4 size paper.

EXAMPLES 26 to 38

By following the same procedure as Example 1 except that the X-type non-metal phthalocyanine and the ketone compound in Example 1 were changed to the compounds shown in Table 3 below, electrophotographic photosensitive members were prepared and the same evaluations were made on each sample. The results obtained are shown in Table 3 and Table 4 below.

COMPARISON EXAMPLE 2 to 7

By following the same procedures as Examples 32 to 58 except that the ketone compound was not added, electrophotographic photosensitive members were prepared and the same evaluations were made on each sample. The results are shown in Table 3 and Table 4.

TABLE 3

| | Charge Generating Pigment | No. | Amount (equivalent) | 32° C., 85% RH at one cycle | at 200 cycles | 20° C., 55% RH at one cycle | at 200 cycles | 10° C., 15% RH at one cycle | at 200 cycles (Unit: Volt) |
|---|---|---|---|---|---|---|---|---|---|
| | | | Ketone compound (Ia) | | | | | | |
| Example 26 | III-3 | Ia-3 | 0.3 | VH −285<br>VL −77 | −283<br>−76 | −289<br>−81 | −289<br>−81 | −291<br>−84 | −291<br>−83 |
| Example 27 | III-6 | Ia-5 | 0.3 | VH −280<br>VL −74 | −279<br>−74 | −283<br>−78 | −282<br>−77 | −284<br>−79 | −285<br>−80 |
| Example 28 | III-10 | Ia-11 | 0.3 | VH −284<br>VL −80 | −283<br>−79 | −287<br>−82 | −288<br>−82 | −290<br>−83 | −291<br>−83 |
| Example 29 | III-12 | Ia-13 | 0.3 | VH −281<br>VL −91 | −280<br>−90 | −285<br>−99 | −283<br>−96 | −288<br>−103 | −290<br>−105 |
| Example 30 | III-20 | Ia-15 | 0.3 | VH −280<br>VL −79 | −279<br>−79 | −285<br>−84 | −284<br>−84 | −288<br>−87 | −289<br>−87 |
| Example 31 | Vanadyl-phthalocyanine | Ia-22 | 0.3 | VH −239<br>VL −46 | −239<br>−45 | −241<br>−51 | −240<br>−50 | −244<br>−53 | −245<br>−53 |
| | | | Cyanovinyl compound (Id) | | | | | | |
| Example 32 | III-3 | Ib-41 | 0.3 | VH −271<br>VL −72 | −269<br>−70 | −284<br>−79 | −280<br>−78 | −289<br>−88 | −293<br>−92 |
| Example 33 | III-6 | Ib-42 | 0.3 | VH −271<br>VL −70 | −269<br>−66 | −277<br>−76 | −277<br>−74 | −287<br>−92 | −290<br>−84 |
| Example 34 | III-10 | Ib-44 | 0.3 | VH −267<br>VL −72 | −267<br>−69 | −282<br>−81 | −279<br>−80 | −285<br>−87 | −291<br>−92 |
| Example 35 | III-12 | Ib-51 | 0.3 | VH −264<br>VL −92 | −256<br>−90 | −271<br>−100 | −269<br>−95 | −287<br>−108 | −299<br>−108 |
| Example 36 | III-20 | Ib-52 | 0.3 | VH −281<br>VL −79 | −278<br>−75 | −288<br>−83 | −284<br>−82 | −292<br>−88 | −303<br>−88 |
| Example 37 | Vanadyl-phthalocyanine | Ib-53 | 0.3 | VH −231<br>VL −47 | −229<br>−43 | −238<br>−54 | −235<br>−51 | −244<br>−59 | −247<br>−62 |
| Example 38 | ε-Copper phthalocyanine | Ib-54 | 0.3 | VH −267<br>VL −122 | −265<br>−118 | −273<br>−127 | −270<br>−123 | −279<br>−131 | −283<br>−129 |
| Comparison Example 2 | III-3 | — | — | VH −267<br>VL −92 | −241<br>−61 | −290<br>−110 | −282<br>−101 | −301<br>−135 | −303<br>−148 |
| Comparison Example 3 | III-6 | — | — | VH −256<br>VL −89 | −243<br>−58 | −286<br>−107 | −279<br>−98 | −298<br>−131 | −301<br>−139 |
| Comparison Example 4 | III-10 | — | — | VH −261<br>VL −99 | −239<br>−60 | −291<br>−113 | −294<br>−99 | −300<br>−137 | −305<br>−149 |
| Comparison Example 5 | II-12 | — | — | VH −271<br>VL −121 | −261<br>−101 | −291<br>−132 | −285<br>−131 | −300<br>−152 | −306<br>−164 |
| Comparison Example 6 | II-20 | — | — | VH −253<br>VL −92 | −228<br>−66 | −286<br>−114 | −277<br>−109 | −298<br>−137 | −307<br>−149 |
| Comparison Example 7 | Vanadyl-phthalocyanine | — | — | VH −221<br>VL −55 | −190<br>−30 | −245<br>−63 | −238<br>−58 | −277<br>−86 | −282<br>−100 |
| Comparison Example 8 | ε-Copper phthalocyanine | — | — | VH −273<br>VH −146 | −271<br>−122 | −296<br>−157 | −298<br>−141 | −295<br>−178 | −299<br>−161 |

TABLE 4

| | Charge Generating Pigment | No. | Amount (equivalent) | Printout Density Difference Between the Portion Used for A-4 Size Paper and the Widened Portion | Fog at Background Position Portion Used for A-4 Size Paper | Widened Portion by B-4 Size Paper |
|---|---|---|---|---|---|---|
| | | | Ketone compound (Ia) | | | |
| Example 26 | III-3 | Ia-3 | 0.3 | Uniform (no difference) | no fog | no fog |
| Example 27 | III-6 | Ia-5 | 0.3 | " | no fog | no fog |
| Example 28 | III-10 | Ia-11 | 0.3 | " | no fog | no fog |
| Example 29 | III-12 | Ia-13 | 0.3 | " | no fog | no fog |
| Example 30 | III-20 | Ia-15 | 0.3 | " | no fog | no fog |
| Example 31 | Vanadyl-phthalocyanine | Ia-22 | 0.3 | " | no fog | no fog |
| | | | Anthraquinon compound (Ib) | | | |
| Example 32 | III-3 | Ib-41 | 0.3 | Uniform (no difference) | no fog | no fog |
| Example 33 | III-6 | Ib-42 | 0.3 | " | no fog | no fog |
| Example 34 | III-10 | Ib-44 | 0.3 | " | no fog | no fog |
| Example 35 | III-12 | Ib-51 | 0.3 | " | no fog | no fog |
| Example 36 | III-20 | Ib-52 | 0.3 | " | no fog | no fog |
| Example 37 | Vanadyl-phthalocyanine | Ib-53 | 0.3 | " | no fog | no fog |
| Example 38 | ε-Copper phthalocyanine | Ib-54 | 0.3 | " | no fog | no fog |
| Comparison Example 2 | III-3 | — | — | * | no fog | fogged |
| Comparison Example 3 | III-6 | — | — | Uniform (no difference) | no fog | fogged |
| Comparison Example 4 | III-10 | — | — | " | no fog | fogged |
| Comparison Example 5 | III-12 | — | — | " | no fog | no fog |

TABLE 4-continued

| | Charge Generating Pigment | No. | Amount (equivalent) | Printout Density Difference Between the Portion Used for A-4 Size Paper and the Widened Portion | Fog at Background Position | |
|---|---|---|---|---|---|---|
| | | | | | Portion Used for A-4 Size Paper | Widened Portion by B-4 Size Paper |
| Comparison Example 6 | III-20 | — | — | " | no fog | fogged |
| Comparison Example 7 | Vanadyl-phthalocyanine | — | — | " | no fog | fogged |
| Comparison Example 8 | ε-Copper phthalocyanine | — | — | " | no fog | fogged |

EXAMPLES 39 to 53

By following the same procedure as Example 1 except that an aluminum pipe of 84 mm in outside diameter and 310 mm in length subjected to mirror plane cutting was used as the substrate, the perylene pigment (Compound IV-1) was used as the charge generating pigment, and each of the compounds shown in Table 5 was used as the compound of formula (I), electrophotographic photosensitive members were prepared.

Each of the electrophotographic photosensitive members was negatively charged using Scorotron (grid voltage: −300 volts), exposed to a halogen lamp (using an interference filter of 550 n.m. as the center wavelength) to cause light decay, after exposure, a probe of a surface densitometer was placed on the position after 0.3 second (corresponding to the position after 0.6 second since charging), and the potential (VH) for non-exposure and the potential (VL: 30 erg/cm$^2$ exposure) for exposure were measured.

Furthermore, Corotron (wire voltage: +5.0 KV) was disposed at the rear of the probe, the photosensitive member was positive charged, and thereafter the charges were removed by a tungsten lamp. In the system, the step of negative charging-exposure-positive charging-exposure for charge removal was defined as one cycle and the changes of VH and VL upto 200 cycles were measured. The measurement was performed under the surrounding conditions of 32° C., 85% RH, 20° C., 55% RH, and 10° C, 15% RH. The results obtained are shown in Table 5 below.

COMPARISON EXAMPLE 8

By following the same procedure as Example 39 except that the ketone compound was not added, an electrophotographic photosensitive member was prepared and the same evaluations were made. The results are shown in Table 5.

COMPARISON EXAMPLES 9 and 10

By following the same procedure as Example 39 except that dibromoanthanthrone or the bisazo pigment shown by the following structural formula

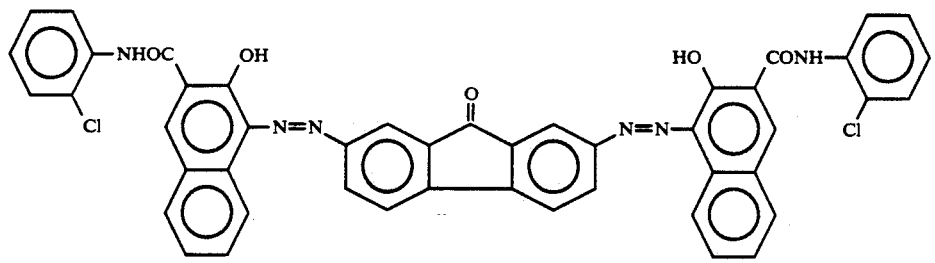

was used in place of the perylene pigment (Compound V-1), electrophotographic photosensitive members were prepared and the same evaluations were made on each sample. The results are shown in Table 5 below.

COMPARISON EXAMPLES 11 and 12

By following the same procedures as Comparison Example 9 and 10 except that the compound of formula (Ib) shown in Table 5 was used in place of the ketone compound of formula (Ia), electrophotographic photosensitive members were prepared and the same evaluations were made on each sample. The results are shown in Table 5.

COMPARISON EXAMPLES 13 and 14

By following the same procedures as Comparison Examples 9 and 10 except that the ketone compound of formula (Ia) was not added, electrophotographic photosensitive members were prepared and the evaluations were made on each sample. The results are shown in Table 5.

TABLE 5

| | Charge Generating Pigment | No. | Amount (equivalent) | | 32° C., 85% RH | | 20° C., 55% RH | | 10° C., 15% RH (Unit: volt) | |
|---|---|---|---|---|---|---|---|---|---|---|
| | | | | | at one cycle | at 200 cycles | at one cycle | at 200 cycles | at one cycle | at 200 cycles |
| | | | Ketone compound (Ia) | | | | | | | |
| Example 39 | V-1 | Ia-21 | 0.3 | VH | −276 | −275 | −279 | −278 | −283 | −285 |
| | | | | VL | −159 | −159 | −162 | −162 | −167 | −168 |
| Example 40 | V-1 | Ia-2 | 0.3 | VH | −282 | −281 | −287 | −285 | −291 | −292 |
| | | | | VL | −160 | −160 | −164 | −163 | −167 | −167 |
| Example 41 | V-1 | Ia-4 | 0.3 | VH | −269 | −269 | −275 | −273 | −279 | −280 |
| | | | | VL | −155 | −154 | −159 | −159 | −163 | −162 |

TABLE 5-continued

| | Charge Generating Pigment | No. | Amount (equivalent) | | 32° C., 85% RH at one cycle | 32° C., 85% RH at 200 cycles | 20° C., 55% RH at one cycle | 20° C., 55% RH at 200 cycles | 10° C., 15% RH at one cycle | 10° C., 15% RH at 200 cycles |
|---|---|---|---|---|---|---|---|---|---|---|
| Example 42 | V-1 | Ia-8 | 0.3 | VH | −268 | −266 | −273 | −273 | −278 | −276 |
| | | | | VL | −154 | −154 | −159 | −158 | −162 | −161 |
| Example 43 | V-1 | Ia-12 | 0.3 | VH | −275 | −272 | −278 | −277 | −284 | −281 |
| | | | | VL | −160 | −157 | −165 | −164 | −168 | −166 |
| Example 44 | V-1 | Ia-17 | 0.3 | VH | −283 | −282 | −287 | −286 | −291 | −293 |
| | | | | VL | −165 | −165 | −169 | −169 | −172 | −174 |
| Example 45 | V-1 | Ia-19 | 0.3 | VH | −275 | −274 | −280 | −280 | −285 | −286 |
| | | | | VL | −161 | −160 | −164 | −163 | −166 | −167 |
| Comparison Example 8 | V-1 | — | — | VH | −271 | −253 | −282 | −273 | −299 | −297 |
| | | | | VL | −166 | −131 | −179 | −171 | −208 | −210 |
| Comparison Example 9 | Dibromo-anthanthrone | Ia-21 | 0.3 | VH | −269 | −251 | −300 | −295 | −301 | −292 |
| | | | | VL | −141 | −132 | −171 | −165 | −186 | −181 |
| Comparison Example 10 | Bisazo pigment | Ia-21 | 0.3 | VH | −232 | −221 | −284 | −273 | −289 | −285 |
| | | | | VL | −69 | −48 | −79 | −66 | −110 | −111 |
| | | Cyanovinyl compound (Ib) | | | | | | | | |
| Example 46 | V-1 | Ib-1 | 0.3 | VH | −271 | −263 | −280 | −275 | −288 | −282 |
| | | | | VL | −163 | −158 | −165 | −165 | −172 | −175 |
| Example 47 | V-1 | Ib-12 | 0.3 | VH | −268 | −264 | −277 | −271 | −280 | −284 |
| | | | | VL | −152 | −150 | −163 | −165 | −178 | −172 |
| Example 48 | V-1 | Ib-20 | 0.3 | VH | −284 | −280 | −292 | −284 | −301 | −288 |
| | | | | VL | −149 | −141 | −157 | −154 | −160 | −152 |
| Example 49 | V-1 | Ib-27 | 0.3 | VH | −257 | −243 | −269 | −260 | −277 | −269 |
| | | | | VL | −140 | −139 | −149 | −144 | −155 | −150 |
| Example 50 | V-1 | Ib-28 | 0.3 | VH | −264 | −259 | −273 | −269 | −282 | −277 |
| | | | | VL | −149 | −140 | −157 | −157 | −163 | −157 |
| Example 51 | V-1 | Ib-31 | 0.3 | VH | −265 | −266 | −270 | −273 | −292 | −299 |
| | | | | VL | −151 | −156 | −159 | −162 | −163 | −169 |
| Example 52 | V-1 | Ib-32 | 0.3 | VH | −277 | −270 | −292 | −281 | −299 | −289 |
| | | | | VL | −152 | −141 | −163 | −161 | −166 | −162 |
| Example 53 | V-1 | Ib-35 | 0.3 | VH | −267 | −266 | −274 | −270 | −281 | −285 |
| | | | | VL | −152 | −145 | −158 | −157 | −163 | −160 |
| Comparison Example 11 | Dibromo-anthanthrone | Ib-1 | 0.3 | VH | −267 | −260 | −282 | −284 | −298 | −290 |
| | | | | VL | −142 | −130 | −171 | −169 | −203 | −192 |
| Comparison Example 12 | Bisazo pigment | Ib-1 | 0.3 | VH | −254 | −242 | −293 | −281 | −299 | −300 |
| | | | | VL | −69 | −39 | −82 | −73 | −110 | −101 |
| Comparison Example 13 | Dibromo-anthanthrone | — | — | VH | −271 | −252 | −298 | −295 | −301 | −284 |
| | | | | VL | −147 | −135 | −170 | −165 | −191 | −198 |
| Comparison Example 14 | Bisazo pigment | — | — | VH | −249 | −238 | −290 | −277 | −294 | −289 |
| | | | | VL | −75 | −43 | −85 | −71 | −113 | −121 |

EXAMPLES 54 and 55 and COMPARISON EXAMPLE 15

Each of the electrophotographic photosensitive members prepared in Examples 1, 12, 23, and 34 and Comparison Example 1 was negatively charged using Scorotron (grid voltage: −300 volts); image-exposed by semiconductor laser (780 n.m. oscillation) to cause light decay; after exposure, a probe of a surface potentiometer was placed on the portion after 0.3 second (corresponding to 0.6 second since charging); and the potential (VH) for non-exposure and the potential (VL: 20 erg/cm² exposure) for exposure were measured. Furthermore, Corotron (wire voltage: −5.0 KV) was disposed at the rear of the probe to negatively charge the photosensitive member and thereafter, the charges were removed by tungsten lamp. In the system, the step of negative-charging exposure, negative-charging exposure for charge removal was defined as one cycle and the changes of VH and VL up to 200 cycles were measured. The measurement was performed under the surrounding conditions of 32° C., 85% RH, 20° C., 55% RH, and 10° C., 15% RH. The results are shown in Table 6 below.

TABLE 6

| | Charge Generating Pigment | Ketone or Cyanovinyl compound No. | Amount (equivalent) | | 32° C., 85% RH at one cycle | 32° C., 85% RH at 200 cycles | 20° C., 55% RH at one cycle | 20° C., 55% RH at 200 cycles | 10° C., 15% RH at one cycle | 10° C., 15% RH at 200 cycles |
|---|---|---|---|---|---|---|---|---|---|---|
| Example 54 | X-Type Non-Metal Phthalocyanine | Ia-10 | 0.3 | VH | −247 | −246 | −249 | −250 | −258 | −258 |
| | | | | VL | −56 | −56 | −58 | −58 | −63 | −62 |
| Example 55 | X-Type Non-Metal Phthalocyanine | Ib-14 | 0.3 | VH | −247 | −238 | −251 | −250 | −268 | −261 |
| | | | | VL | −52 | −48 | −54 | −49 | −57 | −60 |
| Comparison Example 15 | X-Type Non-Metal Phthalocyanine | — | — | VH | −226 | −211 | −257 | −251 | −292 | −299 |
| | | | | VL | −69 | −62 | −88 | −82 | −117 | −120 |

EXAMPLES 56 and 57 and COMPARISON EXAMPLE 16

An aluminum pipe of 85 mm in outside diameter and 310 mm in length subjected to mirror-plane cutting was surface-polished by grinding stone so that the surface roughness Ra became 0.15 μm. Then, by following the same procedures as Examples 1 or 12 and Comparison Example 1 using the aluminum pipe as the substrate, electrophotographic photosensitive members were prepared.

Each of the electrophotographic photosensitive members thus prepared was mounted on a two-color laser printer (operated by repeating the steps of charging, 1st laser exposure, negative-charging red toner development of the unexposed portions, 2nd laser exposure, positive-charging black toner development of the unexposed portions, charging before transfer by AC formed by overlapping DC (square waves), transferring by negative DC Corotron, cleaning, and charge removal) produced by improving a copying machine (FX 2700, trade name, made by Fuji Xerox Co.), 500 prints of red and black patterns were made using B4 size papers, and the changes of the printout densities at the red portions and the black portions were observed.

In the electrophotographic photosensitive members of Examples 56 and 57, clear printouts having red portions and black portions without any fog on the background portion were obtained; but in the electrophotographic photosensitive members of Comparison Example 16, the fog of the red toners in the background portions was increased, the red printout became broader, and black printout became thinner with the increase of the number of the printed papers.

As described above, the electrophotographic photosensitive member of this invention has the charge generating layer containing the charge generating pigment having the positive hole transporting property and the compound of formula (I) (e.g., at least one of the compounds shown by formulae (Ia) and (Ib)) and has the excellent effects that the sensitivity is improved, the charging property is good, the photosensitivity and the charging potential are stable to the changes of surrounding conditions, and the potentials of the exposed portions and unexposed portions are stable without being reduced during making many copies as compared to the case of containing no such components.

The electrophotographic photosensitive member of this invention is particularly suitably applied to the electrophotographic image-forming process comprising the repeating steps of uniform charging, image exposure, reversal development, positive charging transfer, and charge removal, e.g., the case of using a laser printer, etc., and in this case, the surface density of the photosensitive member in the image exposure keeps a relatively stable potential without causing the reduction in potential with a repeated image-forming operation from the initial image-forming step after repeating many times the image-forming step, and hence images having stable image density can be obtained in continuous repeated use and also the formation of fog can be restrained in such a case.

Furthermore, in the case of changing the size of transfer papers to a large size of papers after repeating many times the image-forming operation, the increase of the transfer density at the broadened portions of the new transfer papers and hence images having a uniform density without fog on the background portions can be obtained.

In addition, when the compound of formula (I) is not contained in the charge generating layer 1, the potential of the exposed portions and the unexposed portions is gradually reduced with the repeating operation of the image-forming step, the image density is gradually increased and fog forms at the background portions. Also, in the case of changing the size of transfer papers to a large size paper after repeating many times the image-forming step, the increase of image density and the formation of background fog are observed on the broadened portions of the new transfer papers.

Furthermore, the electrophotographic photosensitive member of this invention can be applied to a so-called one-pass multicolor image-forming process.

While the invention has been described in detail and with reference to specific embodiments thereof, it will be apparent to one skilled in the art that various changes and modifications can be made therein without departing from the spirit and scope thereof.

What is claimed is:

1. An electrophotographic photosensitive member having a charge generating layer and a charge transporting layer successively formed on a support, wherein the charge generating layer has a thickness of from about 0.05 $\mu$m to about 5 $\mu$m and the charge transporting layer has a thickness from about 5 $\mu$m to 50 $\mu$m and wherein the charge generating layer contains (1) a charge generating pigment having a positive hole transporting property, (2) at least one compound having a formula selected from the group consisting of the following formulae (Ia) and (Ib), and (3) a binder resin;

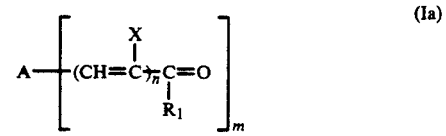

wherein A represents an aromatic group which may be substituted or a heterocyclic group which may be substituted, X represents a hydrogen atom or a halogen atom, $R_1$ represents a hydrogen atom, an alkyl group or a cyano group when n is 0, or a hydrogen atom, an alkyl group, a cyano group or an acryl group when n is 1, n represents 0 or 1, and m represents 1 or 2;

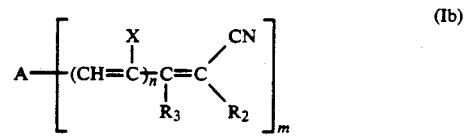

wherein A represents an aromatic group which may be substituted or a heterocyclic group which may be substituted, X represents a hydrogen atom or a halogen atom, $R_2$ represents a cyano group, an aryl group, an alkoxycarbonyl group, or aryloxycarbonyl group, an aminocarbonyl group, an acyl group, a benzoyl group which may be substituted or a phenyl group which may be substituted, $R_3$ represents a hydrogen atom, an alkyl group or a cyano group, n represents 0 or 1, and m represents 1 or 2.

2. The electrophotographic photosenitive member as in claim 1, wherein at least one of the compounds shown by formulae (Ia) and (Ib), is incorporated in the charge generating layer in an amount of from 0.01 to 2 molar equivalents to the charge generating pigment having the positive hole transporting property.

3. The electrophotographic photosenitive member as in claim 1, wherein the charge generating pigment having the positive hole transporting property is a phthalocyanine series pigment, a squarylium series pigment, or a perylene series pigment.

4. The electrophotographic photosensitive member as in claim 1, wherein the compound of formula (Ia) has the following formula (IIa):

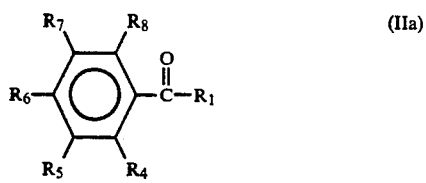

wherein $R_1$ represents a hydrogen atom, an alkyl group or a cyano group, and $R_4$, $R_5$, $R_6$, $R_7$, and $R_8$ each represents a hydrogen atom, an alkyl group, an alkoxy group, an aryloxy group, an aryl group, an alkenyl group, an alkoxycarbonyl group, an aryloxycarbonyl group, an alkylcarbonyl group, an arylcarbonyloxy group, a halogen atom, a cyano group or a nitro group, or two of $R_4$ to $R_8$ which are adjacent to each other to form an aromatic ring or a heterocyclic ring.

5. The electrophotographic photosensitive member as in claim 1, wherein the compound of formula (Ib) has the following formula (IIb):

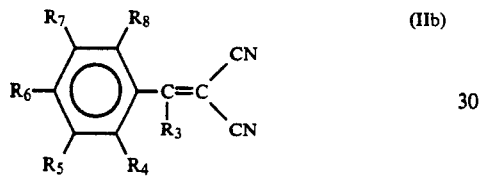

wherein $R_3$ represents a hydrogen atom, an alkyl group or a cyano group, and $R_4$, $R_5$, $R_6$, $R_7$, and $R_8$ each represents a hydrogen atom, an alkyl group, an alkoxy group, an aryloxy group, an aryl group, an alkenyl group, an alkoxycarbonyl group, an alkylcarbonyloxy group, an arylcarbonyloxy group, a halogen atom, a cyano group or a nitro group, or an atomic group necessary for forming an aromatic ring or a heterocyclic ring by combining two of $R_4$ to $R_8$ which are adjacent to each other.

6. The electrophotographic photosensitive member having a charge generating layer and a charge transporting layer successively formed on a support, as claimed in claim 2, wherein, in the charge generating layer, the charge generating pigment having the hole transporting property is incorporated in said charge generating layer in a range from 0.1 to 10 parts by weight to one part by weight of the binder resin, said pigment being dispersed in said charge-generating layer as particles of said pigment of mean size not greater than 3 μm.

7. The electrophotographic photosensitive member having a charge generating layer and a charge transporting layer successively formed on a support, as claimed in claim 1, additionally including a protective layer formed over said successively formed layers.

8. The electrophotographic photosensitive member as in claim 1, wherein the charge generating layer has a thickness of a value from about 0.1 μm to about 2.0 μm.

9. The electrophotographic photosensitive member as in claim 1, wherein the charge transporting layer has a thickness of a value from about 10 μm to about 30 μm.

10. The electrophotographic photosensitive member as in claim 1, wherein the compound represented by formula (Ia) or (Ib) is present in the charge generating layer in an amount from about 0.1 to about 1 molar equivalent of the amount of the charge generating pigment having the positive hole transporting property.

11. The electrophotographic photosensitive member as in claim 1, wherein said charge transporting layer comprises a charge transporting material and a binder at a weight ratio from about 10.:1 to about 1:5.

12. The electrophotographic photosensitive member as in claim 1, wherein said charge generating layer further contains a binder resin.

13. The electrophotographic photosensitive member of claim 12, where said binder resin is selected from the group consisting of polystyrene, silicone polycarbonate, acrylic, methacylio, polyester, vinyl, cellulose and alkyd resins.

14. The electrophotographic photosensitive member as in claim 1, wherein said compound has the formula

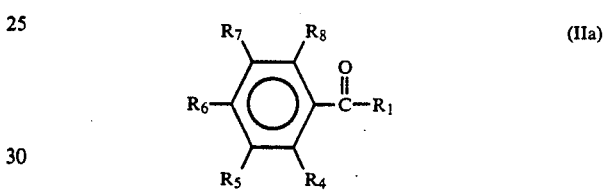

wherein $R_1$ represents a hydrogen atom, an alkyl group or a cyano group, and $R_4$, $R_5$, $R_6$, $R_7$, and $R_8$ each represents a hydrogen atom, an alkyl group, an alkoxy group, an aryloxy group, an aryl group, an alkenyl group, an alkoxycarbonyl group, an aryloxycarbonyl group, an alkylcarbonyl group, an arylcarbonyloxy group, a halogen atom, a cyano group or a nitro group, or two of $R_4$ to $R_8$ which are adjacent to each other to form an aromatic ring or a heterocyclic ring.

15. The electrophotographic photosensitive member as in claim 1 wherein said compound has the formula

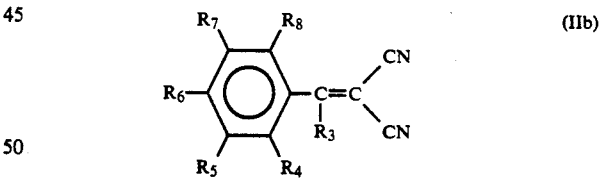

wherein $R_3$ represents a hydrogen atom, an alkyl group or a cyano group, and $R_4$, $R_5$, $R_6$, $R_7$, and $R_8$ each represents a hydrogen atom, an alkyl group, an alkoxy group, an aryloxy group, an aryl group, an alkenyl group, an alkoxycarbonyl group, an alkylcarbonyloxy group, an arylcarbonyloxy group, a halogen atom, a cyano group or a nitro group, or an atomic group necessary for forming an aromatic ring or a heterocyclic ring by combining two of $R_4$ to $R_8$ which are adjacent to each other.

* * * * *

UNITED STATES PATENT AND TRADEMARK OFFICE
CERTIFICATE OF CORRECTION

Page 1 of 2

PATENT NO. : 5,085,960
DATED : February 04, 1992
INVENTOR(S) : Yutaka Akasaki et al.

It is certified that error appears in the above-identified patent and that said Letters Patent is hereby corrected as shown below:

Abstract, lines 10 and 11, change "charge-supporting" to read --charge-transporting--.

Claim 2, column 46, line 58, change "photosenitive" to --photosensitive--.

Claim 2, column 46, line 60, after "(Ib)" delete ",".

Claim 3, column 46, line 64, change "photosenitive" to --photosensitive--.

UNITED STATES PATENT AND TRADEMARK OFFICE
CERTIFICATE OF CORRECTION

PATENT NO. : 5,085,960

DATED : February 4, 1992

INVENTOR(S) : Yutaka Akasaki, et al.

It is certified that error appears in the above-identified patent and that said Letters Patent is hereby corrected as shown below:

Claim 13, column 48, line 20, change "methacylio" to read --methacrylic--.

Signed and Sealed this

Fifteenth Day of June, 1993

Attest:

MICHAEL K. KIRK

*Attesting Officer*     *Acting Commissioner of Patents and Trademarks*